(12) United States Patent
Pierzynowski

(10) Patent No.: US 9,592,211 B2
(45) Date of Patent: Mar. 14, 2017

(54) COMPOSITIONS FOR IMPROVEMENT OF BRAIN FUNCTION

(71) Applicant: GRESPO AB, Stockholm (SE)

(72) Inventor: Stefan Pierzynowski, Trelleborg (SE)

( * ) Notice: Subject to any disclaimer, the term of this patent is extended or adjusted under 35 U.S.C. 154(b) by 0 days.

(21) Appl. No.: 14/428,841

(22) PCT Filed: Sep. 19, 2013

(86) PCT No.: PCT/SE2013/051098
§ 371 (c)(1),
(2) Date: Mar. 17, 2015

(87) PCT Pub. No.: WO2014/046603
PCT Pub. Date: Mar. 27, 2014

(65) Prior Publication Data
US 2015/0297544 A1   Oct. 22, 2015

Related U.S. Application Data

(60) Provisional application No. 61/703,163, filed on Sep. 19, 2012.

(30) Foreign Application Priority Data

Sep. 19, 2012   (SE) ...................... 1200567

(51) Int. Cl.
| | |
|---|---|
| *A61K 38/54* | (2006.01) |
| *A61K 38/46* | (2006.01) |
| *A61K 31/194* | (2006.01) |
| *A61K 38/48* | (2006.01) |
| *A61K 38/47* | (2006.01) |
| *A61K 31/198* | (2006.01) |

(52) U.S. Cl.
CPC .......... *A61K 31/194* (2013.01); *A61K 31/198* (2013.01); *A61K 38/465* (2013.01); *A61K 38/47* (2013.01); *A61K 38/48* (2013.01); *A61K 38/54* (2013.01); *C12Y 302/01001* (2013.01)

(58) Field of Classification Search
CPC .............................. A61K 38/54; A61K 38/46
See application file for complete search history.

(56) References Cited

U.S. PATENT DOCUMENTS

| | | | |
|---|---|---|---|
| 6,537,969 B1 | 3/2003 | Blass | |
| 2002/0177213 A1 | 11/2002 | Moore et al. | |
| 2003/0040542 A1 | 2/2003 | Martin | |
| 2003/0165457 A1 | 9/2003 | Martin | |
| 2004/0081681 A1 | 4/2004 | Vromen | |
| 2008/0279786 A1 | 11/2008 | Cash | |
| 2010/0092447 A1* | 4/2010 | Fallon ................... | A61K 38/47 424/94.2 |
| 2010/0124537 A1 | 5/2010 | Kruszewska | |
| 2011/0064712 A1 | 3/2011 | Amato | |

FOREIGN PATENT DOCUMENTS

| | | | |
|---|---|---|---|
| CA | 2597395 A1 | 8/2006 | |
| CN | 1281283 C | 10/2006 | |
| CN | 101884631 A | 11/2010 | |
| EP | WO 2007/082914 A2 * | 7/2007 | ............. A61P 19/00 |
| EP | 1915913 A1 | 4/2008 | |
| JP | H08225460 | 9/1996 | |
| WO | WO2006016828 A2 | 2/2006 | |
| WO | WO2006066244 A2 | 6/2006 | |
| WO | WO2007082914 | 7/2007 | |
| WO | WO2010002972 A1 | 1/2010 | |
| WO | WO2010132502 | 11/2010 | |
| WO | WO2011163319 A2 | 12/2011 | |
| WO | WO2012025921 A1 | 3/2012 | |
| WO | WO2012078798 A1 | 6/2012 | |

* cited by examiner

*Primary Examiner* — Scott Long
*Assistant Examiner* — Natalie Moss
(74) *Attorney, Agent, or Firm* — Zareefa B. Flener; Flener IP Law

(57) ABSTRACT

A composition comprising alpha-ketoglutaric acid or a pharmaceutically acceptable salt thereof (AKG), and one or more enzymes selected from a group consisting of a lipase, a protease and an amylase, and medical uses thereof in, neurological and/or neurodegenerative disease, neurological trauma, depression or chronic fatigue syndrome.

7 Claims, 9 Drawing Sheets

COMPOSITIONS FOR IMPROVEMENT OF BRAIN FUNCTION

FIELD OF THE INVENTION

The present invention relates to the field of medicine and nutraceuticals, in particular the treatment of neurological and/or neurodegenerative disorders and improvement of brain function.

BACKGROUND

It has been known for some time now that formation of new neurons from neural stem cells (neurogenesis) continues throughout life in adult mammals including humans, although it has a clear tendency to decrease with age. One of the most active loci for adult neurogenesis is the hippocampus, which has a crucial role in memory and spatial navigation. Hippocampus is also one of the first regions suffering damage in Alzheimer's disease. Stimulation of adult neurogenesis has been subject to intensive research pursuing the hypothesis that a number of neurological disorders (in particular neurodegenerative disorders such as Parkinson's or Alzheimer's as well as depression) might be treatable in such manner.

Eosinophils (or eosinophil granulocytes) are white blood cells involved in defense against parasites, but are also involved in many neoplastic, autoimmune and allergic diseases. There are a number of treatments that lower eosinophile numbers, such as corticosteroids, mepoluzimab, reslizumab, leukotriene antagonists and imatinib, none of which is without drawbacks.

There is considerable unmet medical need for alternative and/or improved treatments of disorders involving eosinophilia, neurological and/or neurodegenerative disorders and for improvement of brain function.

It is an object of the present invention to provide such treatments and means for such treatments.

DEFINITIONS

Throughout this application, unless specifically stated otherwise, the abbreviation AKG refers to alpha-ketoglutaric acid (see Formula I):

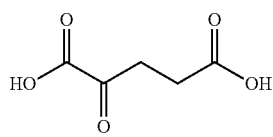

Formula I as well as any pharmaceutically acceptable salts thereof. Such salts of the invention may be inorganic or organic. Examples of preferable salts include sodium and calcium salts of alpha-ketoglutaric acid (denoted Na-AKG and Ca-AKG, respectively). Other preferable salts include potassium-AKG and magnesium-AKG as well as organic salts of alpha-ketoglutaric acid where the counter-ion is an amino-acid naturally occurring in proteins (such as arginine, leucine, isoleucine), pyridoxine, chitosan, creatine or ornithine.

The term pharmaceutically acceptable salt encompasses any salts that are pharmaceutically acceptable in the sense that they are not toxic to the intended subject at the doses intended and are sufficiently stable and soluble for the intended purpose. Preferably, the counter-ion of alpha-ketoglutarate in a pharmaceutically acceptable salt of the invention is not an active ingredient by itself, although it may in some cases be acceptable that the counter-ion is an active ingredient.

The term lipase in the context of the present invention refers to enzymes that catalyze the hydrolytic release of fatty acids from triglycerides releasing fatty acids and glycerol, monoglycerides and/or diglycerides. Preferably, a lipase catalyzes the release of long-chain or medium-chain polyunsaturated fatty acid (PUFA). In this context "long-chain" may refer to fatty acids having tails longer than 12 carbons and "medium-chain" to fatty acids having tails of 6-12 carbons. By polyunsaturated it is meant that there are at least two double bonds between the carbon atoms in the tail of polyunsaturated fatty acids. Examples of PUFA include but are not limited to linoleic acid, linoelaidic acid, α-linolenic acid, arachidonic acid, eicosapentaenoic acid and docosahexaenoic acid. It is preferable that the activity of the lipase of the present invention is substantially independent of pH and that the lipase is active at a pH 6-8.

The term lipase in the context of the present invention comprises lipases of any origin, including human, animal, plant and fungal, bacterial, eukaryotic and prokaryotic origin, irrespective of if the lipase has been produced by recombinant means or by non-recombinant means.

Preferably, the lipase is or has been made acid stable. Such acid stable lipase may be lipase-CLEC (cross-linked enzyme crystals). Such lipase-CLEC crystals and methods of their manufacture are known in the art, for instance from US2006/0121017, incorporated herein by reference. It is also possible to use non-acid stable lipases if the amount administered is increased to compensate for loss of activity in the stomach, the stomach acidity of the patient reduced by antacids, proton pump inhibitors or other suitable pharmacological means, or if the lipase is formulated in a protective enteric formulation well known in the art.

The term protease in the context of the present invention refers to a proteinase, proteolytic enzyme or peptidase, which is an enzyme that catalyzes the splitting of interior amide peptide bonds in a protein. Specifically, proteases catalyze the conversion of proteins into smaller proteins/peptides and/or their component amino acids by cleaving the amide linkage between the carboxyl group of one amino acid and the amino group of another. Proteases are generally identified by their catalytic type, e.g., aspartic acid peptidases, cysteine (thiol) peptidases, metallopeptidases, serine peptidases, threonine peptidases, alkaline or semi-alkaline proteases, neutral and peptidases of unknown catalytic mechanism (see http://merops.sanger.ac.uk). Any catalytic type is encompassed by the term in the context of the present invention. The term protease in the context of the present invention comprises proteases of any origin, including human, animal, plant and fungal, bacterial, eukaryotic and prokaryotic origin, irrespective of if the protease has been produced by recombinant means or by non-recombinant means.

The term amylase in the context of the present invention refers to amylase enzymes having broad substrate specificity and catalyzing the hydrolysis of α-1,4-glucosidic linkages of starch, glycogen and related polysaccharides containing three or more α-1,4-linked D-glucose units yielding maltose, glucose and/or limit dextrins of 2-3 units. The term amylase in the context of the present invention comprises amylases of any origin, including human, animal, plant and fungal, bacterial, eukaryotic and prokaryotic origin, irrespective of if the amylase has been produced by recombinant means or by non-recombinant means.

The term "USP Unit" refers to the United States Pharmacopoeia unit of enzyme activity present in an agent or composition. One USP Unit of lipase, protease or amylase is defined in Pancrelipase, USP, U.S. Pharmacopeia National Formulary, USP 24, pp. 1254-1255 (2000).

Assays for lipase, protease and amylase are disclosed in that reference and are incorporated herein by reference.

The term neurogenesis in the context of the present invention is taken to mean the process by which new neurons are formed from neural stem cells. In neurogenesis, there is active production of new neurons, astrocytes, glia, and other neural lineages from undifferentiated neural progenitor or stem cells.

The term neurodegenerative disease in the context of the present invention is an umbrella term for any disease causing progressive loss of structure and/or function of neurons, with or without death of neurons. Examples of neurodegenerative diseases include but are not limited to Alzheimer's disease, Parkinson's disease, Huntington's disease and amyotrophic lateral sclerosis.

The term eosinophilia in the context of the present invention encompasses both primary eosinophilia, as well as conditions where increased eosinophile numbers are a symptom.

The term pancrelipase in the context of the present invention encompasses not only pancrelipase according to the normal meaning of the term in the art, but even similar preparations such as pancreatin, and similar preparations from any animal source.

BRIEF DESCRIPTION OF THE DRAWINGS

For explanation on the groups, please see Table 1 and Example 1.

FIG. 3 illustrates results from blood chemistry.

SUMMARY OF THE INVENTION

Figure 1:
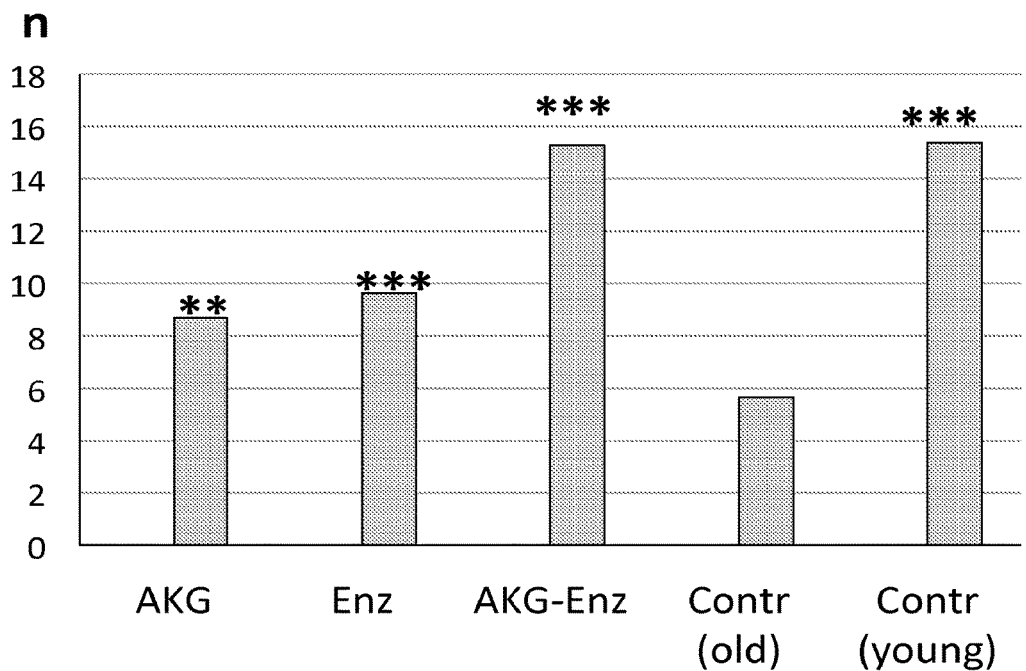
FIG. 1 illustrates increased adult neurogenesis detected by increased number of nestin-positive neurons per 1 mm of pyramidal layer length in hippocampal CA1 area by means of the present invention. Asterisks indicate statistically significant differences.

The present invention provides the following items.
1. A composition comprising alpha-ketoglutaric acid or a pharmaceutically acceptable salt thereof (AKG), and one or more enzymes selected from the group consisting of lipases, proteases and amylases.
2. The composition according to item 1, comprising a lipase, a protease and/or an amylase in an amount according to an embodiment indicated in Table X with reference to Tables Y and Z.
3. The composition according to item 1 or 2, comprising a lipase.
4. The composition according to item 3, wherein the lipase is a mammalian lipase.
5. The composition according to item 3, wherein the lipase is a microbial lipase.
6. The composition according to item 3, wherein the lipase is a bacterial lipase.
7. The composition according to item 3, wherein the lipase is a pancrelipase lipase.
8. The composition according to item 3, wherein the lipase is a liprotamase lipase.
9. The composition according to item 3 wherein the lipase is a *Pseudomonas* lipase.
10. The composition according to item 3, wherein the lipase is a human or other mammalian bile-salt stimulated lipase (BSSL), preferably human.
11. The composition according to item 3, wherein the lipase is a human or other mammalian bile-salt dependent lipase (BSDL), preferably human.
12. The composition according to item 3, wherein the lipase is a *Rhizopus oryzae* lipase.
13. The composition according to item 3, wherein the lipase is a *Chromobacterium viscosum* lipase.
14. The composition according to item 3, wherein the lipase is a *Rhizopus delemar* lipase.
15. The composition according to item 3, wherein the lipase is a *Burkholderia* lipase.
16. The composition according to item 15, wherein the lipase is a *Burkholderia cepacia* lipase.

17. The composition according to item 16, wherein the lipase is a *Burkholderia cepacia* lipase as cross-linked lipase crystals.
18. The composition according to any of items 1-17, comprising a protease.
19. The composition according to item 18, wherein the protease is a mammalian protease.
20. The composition according to item 18, wherein the protease is a microbial protease.
21. The composition according to item 18, wherein the protease is a fungal protease.
22. The composition according to item 18, wherein the protease is a pancrelipase protease.
23. The composition according to item 18, wherein the protease is a liprotamase protease
24. The composition according to item 18, wherein the protease is an *Aspergillus* protease.
25. The composition according to item 24, wherein the protease is an *Aspergillus melleus* protease.
26. The composition according to any of items 1-25 comprising an amylase.
27. The composition according to item 26, wherein the amylase is a mammalian amylase.
28. The composition according to item 26, wherein the amylase is a microbial amylase.
29. The composition according to item 26, wherein the amylase is a fungal amylase.
30. The composition according to item 26, wherein the amylase is a pancrelipase amylase.
31. The composition according to item 26, wherein the amylase is a liprotamase amylase.
32. The composition according to item 26, wherein the amylase is an *Aspergillus* amylase.
33. The composition according to item 32, wherein the amylase is *Aspergillus oryzae* amylase.
34. The composition according to any of items 1-17, wherein the composition comprises 200-20000 USP units of lipase per mmol AKG.
35. The composition according to any of items 18-25 or 34, wherein the composition comprises 500-50000 USP units of protease per mmol AKG.
36. The composition according to any of items 26-33 or 34-35 wherein the composition comprises 200-20000 USP units of amylase per mmol AKG.
37. The composition according to item 1, comprising 3000-300000 USP units of *Burkholderia cepacia* lipase per g AKG as cross-linked lipase crystals, 2000-200000 USP units of *Aspergillus melleus* protease per g AKG and 300-30000 USP units of *Aspergillus oryzae* amylase per g AKG.
38. The composition according to item 1, comprising liprotamase in an amount corresponding to 300-300000 USP lipase units of liprotamase per g AKG.
39. The composition according to item 1, comprising pancrelipase in an amount corresponding to 300-300000 USP lipase units of pancrelipase per g AKG.
40. The composition according to any of the preceding items, wherein the composition comprises sodium alpha-ketoglutarate.
41. The composition according to any of the preceding items, wherein the composition comprises calcium alpha-ketoglutarate.
42. The composition according to any of the preceding items, for use as a medicament.
43. The composition according to any of the preceding items, for use in the treatment or prevention of a neurological disorder selected from neurodegenerative disorders, neural stem cell disorders, neural progenitor disorders, ischemic disorders, neurological traumas, affective disorders, neuropsychiatric disorders, degenerative diseases of the retina, retinal injury/trauma and cognitive, learning and memory disorders.
44. The composition according to any of the preceding items, for use in the treatment or prevention of a condition selected from: Alzheimer's disease, mild cognitive impairment (MCI), Parkinson's disease and Parkinsonian disorders, Huntington's disease, Amyotrophic Lateral Sclerosis, ischemic stroke, traumatic brain injury, depression, bipolar depression/disorder, chronic fatigue syndrome, anxiety syndromes/disorders, autism, Asperger's syndrome, attention deficit disorders, and disorders of cognitive performance or memory.
45. The composition for use according to item 44, for use in the treatment or prevention of depression or chronic fatigue syndrome.
46. The composition according to any of the preceding items, for use in a method comprising administering an amount of the composition containing 0.1-30 g AKG to a patient per day.
47. The composition according to any of items 1-45, for use in a method comprising administering to a human patient an amount of the composition containing 0.5-240 mmol AKG.
48. The composition according to item 47, for use in a method comprising administering an amount of the composition containing 0.5-24 mmol AKG to a patient per day.
49. The composition according to item 48, for use in a method comprising administering an amount of the composition containing 1-12 mmol AKG to a patient per day.
50. Alpha-ketoglutaric acid or a pharmaceutically acceptable salt thereof, for use in the treatment or prevention of depression or chronic fatigue syndrome.
51. Alpha-ketoglutaric acid or a pharmaceutically acceptable salt thereof, for use in a method of treatment or prevention of neurodegenerative disorders, neural stem cell disorders, neural progenitor disorders, ischemic disorders, neurological traumas, affective disorders, neuropsychiatric disorders, degenerative diseases of the retina, retinal injury/trauma and cognitive, learning and memory disorders, Alzheimer's disease, mild cognitive impairment (MCI), Parkinson's disease and Parkinsonian disorders, Huntington's disease, Amyotrophic Lateral Sclerosis, ischemic stroke, traumatic brain injury, depression, bipolar depression/disorder, chronic fatigue syndrome, anxiety syndromes/disorders, autism, Asperger's syndrome, attention deficit disorders, and disorders of cognitive performance or memory,
the method comprising administering alpha-ketoglutaric acid or a pharmaceutically acceptable salt thereof and one or more enzymes selected from a lipase, a protease and an amylase thereof to a subject.
52. Alpha-ketoglutaric acid or a pharmaceutically acceptable salt thereof, for use according to item 51, wherein the method comprises administering an amount of a lipase, a protease and/or an amylase relative to the amount AKG according to any of the embodiments indicated in Table X with reference to Tables Y and Z.
53. Alpha-ketoglutaric acid or a pharmaceutically acceptable salt thereof, for use according to item 51 or 52, wherein the method comprises administering a lipase.
54. Alpha-ketoglutaric acid or a pharmaceutically acceptable salt thereof, for use according to item 53, wherein the lipase is a mammalian lipase.

55. Alpha-ketoglutaric acid or a pharmaceutically acceptable salt thereof, for use according to item 53, wherein the lipase is a microbial lipase.
56. Alpha-ketoglutaric acid or a pharmaceutically acceptable salt thereof, for use according to item 53, wherein the lipase is a bacterial lipase.
57. Alpha-ketoglutaric acid or a pharmaceutically acceptable salt thereof, for use according to item 53, wherein the lipase is a pancrelipase lipase.
58. Alpha-ketoglutaric acid or a pharmaceutically acceptable salt thereof, for use according to item 53, wherein the lipase is a liprotamase lipase.
59. Alpha-ketoglutaric acid or a pharmaceutically acceptable salt thereof, for use according to item 53, wherein the lipase is a *Pseudomonas* lipase.
60. Alpha-ketoglutaric acid or a pharmaceutically acceptable salt thereof, for use according to item 53, wherein the lipase is a human or other mammalian bile-salt stimulated lipase (BSSL), preferably human.
61. Alpha-ketoglutaric acid or a pharmaceutically acceptable salt thereof, for use according to item 53, wherein the lipase is a human or other mammalian bile-salt dependent lipase (BSDL), preferably human.
62. Alpha-ketoglutaric acid or a pharmaceutically acceptable salt thereof, for use according to item 53, wherein the lipase is a *Rhizopus oryzae* lipase.
63. Alpha-ketoglutaric acid or a pharmaceutically acceptable salt thereof, for use according to item 53, wherein the lipase is a *Chromobacterium viscosum* lipase.
64. Alpha-ketoglutaric acid or a pharmaceutically acceptable salt thereof, for use according to item 53, wherein the lipase is a *Rhizopus delemar* lipase.
65. Alpha-ketoglutaric acid or a pharmaceutically acceptable salt thereof, for use according to item 53, wherein the lipase is a *Burkholderia* lipase.
66. Alpha-ketoglutaric acid or a pharmaceutically acceptable salt thereof, for use according to item 65, wherein the lipase is a *Burkholderia cepacia* lipase.
67. Alpha-ketoglutaric acid or a pharmaceutically acceptable salt thereof, for use according to item 66, wherein the lipase is a *Burkholderia cepacia* lipase as cross-linked lipase crystals.
68. Alpha-ketoglutaric acid or a pharmaceutically acceptable salt thereof, for use according to any of items 51-67, wherein the method comprises administering a protease.
69. Alpha-ketoglutaric acid or a pharmaceutically acceptable salt thereof, for use according to item 68, wherein the protease is a mammalian protease.
70. Alpha-ketoglutaric acid or a pharmaceutically acceptable salt thereof, for use according to item 68, wherein the protease is a microbial protease.
71. Alpha-ketoglutaric acid or a pharmaceutically acceptable salt thereof, for use according to item 68, wherein the protease is a fungal protease.
72. Alpha-ketoglutaric acid or a pharmaceutically acceptable salt thereof, for use according to item 68, wherein the protease is a pancrelipase protease.
73. Alpha-ketoglutaric acid or a pharmaceutically acceptable salt thereof, for use according to item 68, wherein the protease is a liprotamase protease
74. Alpha-ketoglutaric acid or a pharmaceutically acceptable salt thereof, for use according to item 68, wherein the protease is an *Aspergillus* protease.
75. Alpha-ketoglutaric acid or a pharmaceutically acceptable salt thereof, for use according to item 74, wherein the protease is an *Aspergillus melleus* protease.
76. Alpha-ketoglutaric acid or a pharmaceutically acceptable salt thereof, for use according to any of items 51-75, wherein the method comprises administering an amylase.
77. Alpha-ketoglutaric acid or a pharmaceutically acceptable salt thereof, for use according to item 76, wherein the amylase is a mammalian amylase.
78. Alpha-ketoglutaric acid or a pharmaceutically acceptable salt thereof, for use according to item 76, wherein the amylase is a microbial amylase.
79. Alpha-ketoglutaric acid or a pharmaceutically acceptable salt thereof, for use according to item 76, wherein the amylase is a fungal amylase.
80. Alpha-ketoglutaric acid or a pharmaceutically acceptable salt thereof, for use according to item 76, wherein the amylase is a pancrelipase amylase.
81. Alpha-ketoglutaric acid or a pharmaceutically acceptable salt thereof, for use according to item 76, wherein the amylase is a liprotamase amylase.
82. Alpha-ketoglutaric acid or a pharmaceutically acceptable salt thereof, for use according to item 76, wherein the amylase is an *Aspergillus* amylase.
83. Alpha-ketoglutaric acid or a pharmaceutically acceptable salt thereof, for use according to item 82, wherein the amylase is *Aspergillus oryzae* amylase.
84. Alpha-ketoglutaric acid or a pharmaceutically acceptable salt thereof, for use according to any of items 51-83, wherein the method comprises administering 200-20000 USP units of lipase per mmol AKG.
85. Alpha-ketoglutaric acid or a pharmaceutically acceptable salt thereof, for use according to any of items 51-84, wherein the method comprises administering 500-5000 USP units of protease per mmol AKG.
86. Alpha-ketoglutaric acid or a pharmaceutically acceptable salt thereof, for use according to any of items 51-85, wherein the method comprises administering 200-20000 USP units of amylase per mmol AKG.
87. Alpha-ketoglutaric acid or a pharmaceutically acceptable salt thereof, for use according to item 51, wherein the method comprises administering 3000-300000 USP units of *Burkholderia cepacia* lipase per g AKG as cross-linked lipase crystals, 2000-200000 USP units of *Aspergillus melleus* protease per g AKG and 300-30000 USP units of *Aspergillus oryzae* amylase per g AKG.
88. Alpha-ketoglutaric acid or a pharmaceutically acceptable salt thereof, for use according to item 51, wherein the method comprises administering liprotamase in an amount corresponding to 300-300000 USP lipase units of liprotamase per g AKG.
89. Alpha-ketoglutaric acid or a pharmaceutically acceptable salt thereof, for use according to item 51, wherein the method comprises administering pancrelipase in an amount corresponding to 300-300000 USP lipase units of pancrelipase per g AKG.
90. Alpha-ketoglutaric acid or a pharmaceutically acceptable salt thereof, for use according to any of items 51-89, wherein the method comprises administering sodium alpha-ketoglutarate.
91. Alpha-ketoglutaric acid or a pharmaceutically acceptable salt thereof, for use according to any of items 51-90, wherein the method comprises administering calcium alpha-ketoglutarate.
92. Alpha-ketoglutaric acid or a pharmaceutically acceptable salt thereof, for use according to any of items 51-91, wherein the method comprises administering AKG to the subject at 0.03-100 g/day.
93. Alpha-ketoglutaric acid or a pharmaceutically acceptable salt thereof, for use according to any of items 51-91, wherein the method comprises administering 0.5-240 mmol AKG per day to the subject.
94. Alpha-ketoglutaric acid or a pharmaceutically acceptable salt thereof, for use according item 93, wherein the method comprises administering 0.5-24 mmol AKG per day to the subject.
95. Alpha-ketoglutaric acid or a pharmaceutically acceptable salt thereof, for use according to item 94, wherein the method comprises administering 1-12 mmol AKG per day to the subject.
96. Alpha-ketoglutaric acid or a pharmaceutically acceptable salt thereof, for use according to item 95, wherein the method comprises administering 3-9 mmol AKG per day to the subject.

DETAILED DESCRIPTION

The inventors have found that AKG as well as a composition comprising lipase, protease and amylase had effects in neurogenesis and cognition. A combination of AKG and said enzymes had a synergistic effect in neurogenesis and in improving cognition. The combination also has a synergistic effect on synaptic morphology.

Synergistic Compositions

In a first aspect, the present invention discloses novel synergistic compositions comprising alpha-ketoglutaric acid or a pharmaceutically acceptable salt thereof (AKG), and one or more enzymes selected from a group consisting of a lipase, a protease and an amylase, the constituents being present at synergistically effective relative amounts.

Such compositions have synergistic effect in promoting neurogenesis, improving synaptic morphology and reducing eosinophil counts, enabling treatment of a number of conditions as explained in more detail below.

In certain embodiments, the composition comprises a lipase but no protease or amylase.

In certain embodiments, the composition comprises a protease but no lipase or amylase.

In certain embodiments, the composition comprises an amylase but no protease or lipase.

In certain embodiments, the composition comprises a lipase and a protease but no amylase.

In certain embodiments, the composition comprises a lipase and an amylase but no protease.

In certain embodiments, the composition comprises a protease and an amylase but no lipase.

In certain embodiments, the composition comprises a lipase, a protease, and an amylase.

Lipases, proteases and amylases (and combinations thereof) suitable for use in the composition of the invention are known in the art, see for instance US2006/012017, US2004/0057944, US2001/0046493 and U.S. Pat. No. 6,051,220, all incorporated herein by reference.

The composition may further comprise pharmaceutically or nutritionally acceptable excipients or additives. Optionally, the composition may include additional active ingredients. Preferably, the composition does not include additional active ingredients.

The composition is preferably for oral administration. It may be formulated in any manner well known in the art for oral administration of the substances that it comprises. If the formulation comprises non-acid stable lipase, it may be preferable to encapsulate at least this component in a protective enteric coating. Such coatings are well known in the art and found in products already in the market.

The composition may be a food supplement, a nutraceutical, a pharmaceutical composition, a dietary supplement or a food additive.

Lipase

The composition is the first aspect may comprise a lipase, optionally in combination with a protease as described below, an amylase as described below or both. The lipase may be selected from a mammalian lipase, a microbial lipase, a bacterial lipase, a pancrelipase lipase (i.e. a lipase included in pancrelipase), a liprotamase lipase (i.e. a lipase included in liprotamase), *Pseudomonas* lipase, human or other mammalian bile-salt stimulated lipase (BSSL) or bile-salt dependent lipase (BSDL), *Rhizopus oryzae* lipase, *Chromobacterium viscosum* lipase, *Rhizopus delemar* lipase, *Burkholderia* lipase, more preferably *Burkholderia cepacia* lipase, most preferably *Burkholderia cepacia* lipase as cross-linked lipase crystals.

The composition may comprise 300-3000000 USP units of lipase per g AKG, preferably 3000-300000 USP units of lipase per g AKG, more preferably 6000-150000 USP units of lipase per g AKG and even more preferably 15000-60000 USP units of lipase per g AKG, and most preferably about 30000 USP units of lipase per g AKG.

Protease

The composition of the first aspect may comprise a protease, optionally in combination with a lipase as described above, an amylase as described below or both. The protease may be selected from a mammalian protease, a microbial protease, a fungal protease, a pancrelipase protease (i.e. a protease included in pancrelipase), a liprotamase protease (i.e. a protease included in pancrelipase), an *Aspergillus* protease, most preferably *Aspergillus melleus* protease.

The composition may comprise 200-2000000 USP units of protease per g AKG, preferably 2000-200000 USP units of protease per g AKG, more preferably 4000-100000 USP units of protease per g AKG and even more preferably 10000-40000 USP units of protease per g AKG, and most preferably about 20000 USP units of protease per g AKG.

Amylase

The composition of the first aspect may comprise an amylase, optionally in combination with a lipase as described above, a protease described above or both. The amylase may be selected from a mammalian amylase, a microbial amylase, a fungal amylase, a pancrelipase amylase (i.e. an amylase included in pancrelipase), a liprotamase amylase (i.e. an amylase included in liprotamase), an *Aspergillus* amylase, most preferably *Aspergillus oryzae* amylase.

The composition may comprise 30.0-3000000 USP units of amylase per g AKG, preferably 300-300000 USP units of amylase per g AKG, more preferably 300-30000 USP units of amylase per g AKG and even more preferably 600-15000 USP units of amylase per g AKG, and most preferably about 3000 USP units of amylase per g AKG.

Certain Preferred Combinations and Variants

The composition of the first aspect may comprise 300-3000000 USP units of *Burkholderia cepacia* lipase per g AKG (preferably as cross-linked lipase crystals), 200-2000000 USP units of *Aspergillus melleus* protease per g AKG and 30.0-3000000 USP units of *Aspergillus oryzae* amylase per g AKG.

The composition of the first aspect may comprise 3000-300000 USP units of *Burkholderia cepacia* lipase per g AKG (preferably as cross-linked lipase crystals), 2000-200000 USP units of *Aspergillus melleus* protease per g AKG and 300-300000 USP units of *Aspergillus oryzae* amylase per g AKG.

The composition of the first aspect may comprise 6000-150000 USP units of *Burkholderia cepacia* lipase per g AKG (preferably as cross-linked lipase crystals), 4000-100000 USP units of *Aspergillus melleus* protease per g AKG and 300-30000 USP units of *Aspergillus oryzae* amylase per g AKG.

The composition of the first aspect may comprise 15000-60000 USP units of *Burkholderia cepacia* lipase per g AKG (preferably as cross-linked lipase crystals), 10000-40000 USP units of *Aspergillus melleus* protease per g AKG and 600-15000 USP units of *Aspergillus oryzae* amylase per g AKG.

The composition of the first aspect may comprise about 30000 USP units of *Burkholderia cepacia* lipase per g AKG (preferably as cross-linked lipase crystals), about 20000 USP units of *Aspergillus melleus* protease per g AKG and about 3000 USP units of *Aspergillus oryzae* amylase per g AKG.

The composition of the first aspect may comprise liprotamase. The amount of liprotamase may be 300-300000 USP lipase units of liprotamase per g AKG, preferably 3000-150000 USP lipase units of liprotamase per g AKG, more preferably 15000-60000 USP lipase units of liprotamase per g AKG and most preferably about 30000 USP lipase units of liprotamase per g AKG. A composition with AKG and liprotamase may comprise Na-AKG and Ca-AKG in equal amounts in terms of weight.

The composition of the first aspect may comprise pancrelipase. The amount of pancrelipase may be 300-300000 USP lipase units of pancrelipase per g AKG, preferably 3000-150000 USP lipase units of pancrelipase per g AKG, more preferably 1500-60000 USP lipase units of pancrelipase per g AKG and most preferably about 30000 USP lipase units of pancrelipase per g AKG. A composition with AKG and pancrelipase may comprise Na-AKG and Ca-AKG in equal amounts in terms of weight.

The present invention also provides further embodiments of the composition of the first aspect in Table X appended after the Examples section. The contents of table X are to be read as follows.

Each line in table X corresponds to an embodiment. From the left, the first column denoted "#" shows the embodiment identification number. The second column from the left denoted "A" shows the lipase concentration range for that embodiment, with reference to tables Y and Z. The third column from the left denoted "B" shows the protease concentration range for that embodiment, with reference to tables Y and Z. The fourth column from the left denoted "C" shows the amylase concentration range for that embodiment, with reference to tables Y and Z.

TABLE Y

| Interpretation of columns A, B and C in Table X: | |
|---|---|
| Value in column A, B or C in Table X | Corresponding amount range |
| 1 | base value/250 to base value times 250 |
| 2 | base value/100 to base value times 100 |
| 3 | base value/25 to base value times 25 |
| 4 | base value/10 to base value times 10 |
| 5 | base value/5 to base value times 5 |
| 6 | base value to base value times 5 |
| 7 | base value/5 to base value |
| 8 | base value to base value times 25 |
| 9 | base value/25 to base value |
| 10 | base value times 0 (=not present) |

It is also contemplated that any of the endpoints of ranges of any embodiment in Table X can be combined with any other endpoint of a range (in the same column) of another embodiment in Table X.

For instance two embodiments with values 2 and 9, respectively, in column A can be combined into any one of four additional embodiments, where amount range is (1) base value/100 to base value, (2) base value to base value times 100, (3) base value/25 to base value times 100 or (4) base value/100 to base value/25.

Any endpoint in an embodiment may also be used to form the endpoint of an open range of an additional embodiment. For instance, value 2 in column A forms basis for an embodiment where the lipase amount is "at least base value/100", and an embodiment where the lipase amount is "at least base value time 100" USP units/mmol AKG. Similarly, value 2 in column A forms basis for an embodiment where the lipase amount is "less than base value/100", and an embodiment where the lipase amount is "less than base value time 100" USP units/mmol AKG.

TABLE Z

| Base values for interpretation of columns A, B and C in Table X (with reference to Table Y) | |
|---|---|
| Feature | Base value (USP units/mmol AKG) |
| Lipase, column A in Table X | 2000 |
| Protease, column B in Table X | 5000 |
| Amylase, column C in Table X | 2000 |

To facilitate understanding of how Table X is to be read, the following example is provided:

Embodiment 53 in Table X corresponds to the following values: Column A=1, Column B=6, Column C=3.

From Table Y it can thus be deduced that embodiment 53 corresponds to lipase amount of base value/250 to base value times 250, protease amount of base value to base value times 5, and amylase amount of base value/25 to base value times 25.

Base values can be found in Table Z, whereby embodiment 53 corresponds to:

Lipase amount: 2000/250 to 2000 times 250 USP units/mmol AKG=8-500,000 USP units lipase/mmol AKG
Protease amount: 5000 to 5000 times 5 USP units/mmol AKG=5,000-25,000 USP units protease/mmol AKG
Amylase amount: 2000/25 to 2000 times 25 USP units/mmol AKG=8-50,000 USP units amylase/mmol AKG Preferably, the embodiments of the first aspect of the invention disclosed in Table X with reference to Tables Z and Y comprise *Burkholderia cepacia* lipase as a lipase (preferably as cross-linked lipase crystals), *Aspergillus melleus* protease a protease and *Aspergillus oryzae* amylase as an amylase, to the extent said lipase, protease and amylase are present in the particular embodiment.

More preferably, the embodiments of the first aspect of the invention disclosed in Table X with reference to Tables Z and Y comprise *Burkholderia cepacia* lipase as the only lipase (preferably as cross-linked lipase crystals), *Aspergillus melleus* protease the only protease and/or *Aspergillus oryzae* amylase as the only amylase, to the extent said lipase, protease and amylase are present in the particular embodiment.

AKG

The AKG component in the composition of the first aspect as disclosed above (including the embodiments in Table X) may consist of or comprise sodium alpha-ketoglutarate, calcium alpha-ketoglutarate or a combination thereof (preferably in equal amounts). The AKG component may also comprise or consist of another pharmaceutically acceptable inorganic salt of AKG including magnesium or potassium alpha-ketoglutarate, or a pharmaceutically acceptable organic salt of AKG, such as ornithine-AKG, arginine-AKG, chitosan-AKG, pyrodoxine-AKG, leucine-AKG, isoleucine-AKG or creatine-AKG, or a combination thereof.

Methods and Uses for the Composition of the First Aspect

In a second aspect, the present invention provides a composition according to the first aspect, for use as a medicament.

Use of a composition according to the first aspect in the manufacture of a medicament is also provided.

Additionally, there is provided a method of treatment or prevention comprising administering to a subject in need thereof a composition according to the first aspect.

In a third aspect, the present invention provides a composition according to the first aspect, for use in the treatment or prevention of a neurological disorder selected from neurodegenerative disorders, neural stem cell disorders, neural progenitor disorders, ischemic disorders, neurological traumas, affective disorders, neuropsychiatric disorders, degenerative diseases of the retina, retinal injury/trauma and cognitive, learning and memory disorders.

Use of a composition according to the first aspect in the manufacture of a medicament for the treatment or prevention of a neurological disorder selected from neurodegenerative disorders, neural stem cell disorders, neural progenitor disorders, ischemic disorders, neurological traumas, affective disorders, neuropsychiatric disorders, degenerative diseases of the retina, retinal injury/trauma and cognitive, learning and memory disorders.

Additionally, there is provided a method of treatment or prevention of a neurological disorder selected from neurodegenerative disorders, neural stem cell disorders, neural progenitor disorders, ischemic disorders, neurological traumas, affective disorders, neuropsychiatric disorders, degenerative diseases of the retina, retinal injury/trauma and cognitive, learning and memory disorders comprising administering to a subject in need thereof a composition according to the first aspect.

In a fourth aspect, the present invention provides a composition according to the first aspect, for use in the treatment or prevention of a condition selected from: Alzheimer's disease, mild cognitive impairment (MCI), Parkinson's disease and Parkinsonian disorders, Huntington's disease, Amyotrophic Lateral Sclerosis, spinal ischemia, ischemic stroke, traumatic brain injury, traumatic spinal cord injury, cancer-related brain/spinal cord injury, schizophrenia and other psychoses, lissencephaly syndrome, depression, bipolar depression/disorder, chronic fatigue syndrome, anxiety syndromes/disorders, phobias, stress and related syndromes, cognitive function disorders, aggression, drug and alcohol abuse, obsessive compulsive behaviour syndromes, seasonal mood disorder, borderline personality disorder, cerebral palsy, life style drug abuse, multi-infarct dementia, Lewy body dementia, age related geriatric dementia, epilepsy and injury related to epilepsy, temporal lobe epilepsy, spinal cord injury, brain injury, brain surgery, trauma related brain/spinal cord injury, including concussion related brain injury, brain injury due to repeated concussion or repeated trauma to the head, and brain injury caused by shock wave from an explosion, anti-cancer treatment related brain/spinal cord tissue injury, infection and inflammation related brain/spinal cord injury, environmental toxin related brain/spinal cord injury, multiple sclerosis, autism, Asperger's syndrome, attention deficit disorders, narcolepsy, sleep disorders, and disorders of cognitive performance or memory.

Use of a composition according to the first aspect in the manufacture of a medicament for the treatment or prevention of a condition selected from those disclosed above for the fourth aspect.

Additionally, there is provided a method of treatment or prevention of a condition selected from those disclosed above for the fourth aspect, comprising administering to a subject in need thereof a composition according to the first aspect.

In a fifth aspect, the present invention provides a composition according to the first aspect, for use in the treatment or prevention of depression or chronic fatigue syndrome.

Use of a composition according to the first aspect in the manufacture of a medicament for the treatment or prevention of depression or chronic fatigue syndrome is also provided.

Additionally, there is provided a method of treatment or prevention of depression or chronic fatigue syndrome comprising administering to a subject in need thereof a composition according to the first aspect.

In a sixth aspect, the present invention provides a composition according to the first aspect, for use in the treatment or prevention of disorders involving eosinophilia.

Use of a composition according to the first aspect in the manufacture of a medicament for the treatment or prevention of disorders involving eosinophilia is also provided.

Additionally, there is provided a method of treatment or prevention of disorders involving eosinophilia comprising administering to a subject in need thereof a composition according to the first aspect.

In a seventh aspect, the present invention provides a composition according to the first aspect, for use in the treatment or prevention of allergic diseases including asthma, atopic dermatitis, eosinophilic esophagitis and rhinoconjunctivitis; autoimmune diseases including primary biliary cirrhosis, Riedel invasive fibrous thyroiditis, dermatomyositis, systemic lupus erythematosus and Sjögren's syndrome; parasite infection-induced eosinophilia including helminth infection-induced eosinophilia; graft-versus-host disease; drug-induced eosinophilia; primary eosinophilia, neoplastic disease-induced eosinophilia including eosinophilia associated with primary cutaneous T-cell lymphoma, Sézary syndrome, Hodgkin's disease, Langerhans cell histiocytosis, thyroid cancer, stomach cancer, liver cancer and bladder cancer.

Use of a composition according to the first aspect in the manufacture of a medicament for the treatment or prevention of conditions disclosed above for the fourth aspect is also provided.

Additionally, there is provided a method of treatment or prevention of conditions disclosed above for the fourth aspect, comprising administering to a subject in need thereof a composition according to the first aspect.

In an eight aspect, there is provided a composition according to the first aspect, for use in a method comprising administering an amount of the composition containing 0.03-100 g AKG to a patient per day, 0.1-30 g AKG to a patient per day, 1-10 g AKG to a patient per day, or 2-6 g AKG to a patient per day.

The eight aspect also provides a composition according to the first aspect, for use in a method comprising administering to a (preferably human) patient daily an amount of the composition containing the following amounts of AKG in mmol: 0.5-240, 1-120, 3-60, 5-36, 9-24, 0.5-3, 0.5-5, 0.5-9, 0.5-12, 1-5, 3-9, 3-12, 3-24, 1-5, 3-5, 1-3, 9-36, about 0.5, about 1, about 3, about 5, about 9, about 12, about 24, about 36, about 60, about 120 or about 240. Any range formed by any combination of the endpoints of the aforementioned ranges is also contemplated.

Said administration may be oral. Said patient may be preferably human, in particular a human in need of such treatment.

There is also provided a use of a composition according to the first aspect in the manufacture of a food supplement, a dietary supplement, a nutraceutical or a food additive. Further, there is provided a use of a composition according to the first aspect as a dietary supplement, a food supplement, a nutraceutical or a food additive.

New Medical Uses for AKG

In a ninth aspect, the present invention provides alpha-ketoglutaric acid or a pharmaceutically acceptable salt thereof, for use in the treatment or prevention of depression or chronic fatigue syndrome.

Use of alpha-ketoglutaric acid or a pharmaceutically acceptable salt thereof in the manufacture of a medicament for the treatment or prevention of depression or chronic fatigue syndrome is also provided.

Additionally, there is provided a method of treatment or prevention of depression or chronic fatigue syndrome comprising administering to a subject in need thereof alpha-ketoglutaric acid or a pharmaceutically acceptable salt thereof, in an effective amount.

The alpha-ketoglutaric acid or a pharmaceutically acceptable salt thereof according to the ninth aspect may be for use in a method comprising administering an amount of the alpha-ketoglutaric acid or a pharmaceutically acceptable salt thereof containing 0.03-100 g AKG to a patient per day, preferably 0.1-30 g AKG to a patient per day, more preferably, 1-10 g AKG to a patient per day, most preferably, 2-6 g AKG to a patient per day.

The alpha-ketoglutaric acid or a pharmaceutically acceptable salt thereof according to the ninth aspect may be for use in a method comprising administering to a (preferably human) patient daily an amount of the composition containing the following amounts of AKG in mmol: 0.5-240, 1-120, 3-60, 5-36, 9-24, 0.5-3, 0.5-5, 0.5-9, 0.5-12, 1-5, 3-9, 3-12, 3-24, 1-5, 3-5, 1-3, 9-36, about 0.5, about 1, about 3, about 5, about 9, about 12, about 24, about 36, about 60, about 120 or about 240. Any range formed by any combination of the endpoints of the aforementioned ranges is also contemplated.

Said administration is preferably oral. Said patient may be human, in particular a human in need of such treatment.

The pharmaceutically acceptable salt may consist of or comprise a pharmaceutically acceptable inorganic salt of AKG such as sodium, calcium, magnesium or potassium alpha-ketoglutarate, or a pharmaceutically acceptable organic salt of AKG, such as ornithine-AKG, arginine-AKG, chitosan-AKG, pyrodoxine-AKG, leucine-AKG, isoleucine-AKG or creatine-AKG, or a combination thereof.

AKG for Use in a Method of Treatment or Prevention

In an tenth aspect, the present invention also provides alpha-ketoglutaric acid or a pharmaceutically acceptable salt thereof, for use in a method of treatment or prevention of neurodegenerative disorders, neural stem cell disorders, neural progenitor disorders, ischemic disorders, neurological traumas, affective disorders, neuropsychiatric disorders, degenerative diseases of the retina, retinal injury/trauma, cognitive, learning and memory disorders, Alzheimer's disease, mild cognitive impairment (MCI), Parkinson's disease and Parkinsonian disorders, Huntington's disease, Amyotrophic Lateral Sclerosis, spinal ischemia, ischemic stroke, traumatic brain injury, traumatic spinal cord injury, cancer-related brain/spinal cord injury, schizophrenia and other psychoses, lissencephaly syndrome, depression, bipolar depression/disorder, chronic fatigue syndrome, anxiety syndromes/disorders, phobias, stress and related syndromes, cognitive function disorders, aggression, drug and alcohol abuse, obsessive compulsive behaviour syndromes, seasonal mood disorder, borderline personality disorder, cerebral palsy, life style drug abuse, multi-infarct dementia, Lewy body dementia, age related geriatric dementia, epilepsy and injury related to epilepsy, temporal lobe epilepsy, spinal cord injury, brain injury, brain surgery, trauma related brain/spinal cord injury, including concussion related brain injury, brain injury due to repeated concussion or repeated trauma to the head, and brain injury caused by shock wave from an explosion, anti-cancer treatment related brain/spinal cord tissue injury, infection and inflammation related brain/spinal cord injury, environmental toxin related brain/spinal cord injury, multiple sclerosis, autism, Asperger's syndrome, attention deficit disorders, narcolepsy, sleep disorders, disorders of cognitive performance or memory, a disorder involving eosinophilia, asthma, atopic dermatitis, eosinophilic esophagitis and rhinoconjunctivitis; autoimmune diseases including primary biliary cirrhosis, Riedel invasive fibrous thyroiditis, dermatomyositis, systemic lupus erythematosus and Sjögren's syndrome; parasite infection-induced eosinophilia including helminth infection-induced eosinophilia; graft-versus-host disease; drug-induced eosinophilia; primary eosinophilia, neoplastic disease-induced eosinophilia including eosinophilia associated with primary cutaneous T-cell lymphoma, Sézary syndrome, Hodgkin's disease, Langerhans cell histiocytosis, thyroid cancer, stomach cancer, liver cancer and bladder cancer, the method comprising administering alpha-ketoglutaric acid or a pharmaceutically acceptable salt thereof and one or more of a lipase, a protease and an amylase to a subject.

In certain embodiments, the method comprises administering a lipase but no protease or amylase.

In certain embodiments, the method comprises administering a protease but no lipase or amylase.

In certain embodiments, the method comprises administering an amylase but no protease or lipase.

In certain embodiments, the method comprises administering a lipase and a protease but no amylase.

In certain embodiments, the method comprises administering a lipase and an amylase but no protease.

In certain embodiments, the method comprises administering a protease and an amylase but no lipase.

In certain embodiments, the method comprises administering a lipase, a protease, and an amylase.

The AKG, the lipase, the protease and the amylase administered in the method referred to in the tenth aspect may have same properties and features as specified for the components of the composition of the first aspect.

The relative and absolute amounts of the AKG, the lipase, the protease and the amylase administered in the method referred to in the tenth aspect may be as specified for the composition of the first aspect and uses thereof.

The method of the tenth aspect may comprise administering AKG to the subject at 0.03-100 g/day, 0.1-30 g per day, 1-10 g per day or 2-6 g per day.

In particular the method of the tenth aspect may comprise administering to a (preferably human) patient daily the following amount of AKG in mmol: 0.5-240, 1-120, 3-60, 5-36, 9-24, 0.5-3, 0.5-5, 0.5-9, 0.5-12, 1-5, 3-9, 3-12, 3-24, 1-5, 3-5, 1-3, 9-36, about 0.5, about 1, about 3, about 5, about 9, about 12, about 24, about 36, about 60, about 120 or about 240. Any range formed by any combination of the endpoints of the aforementioned ranges is also contemplated.

The method referred to in the tenth aspect may comprise administering the AKG, the lipase, the protease and/or the amylase simultaneously, separately or consecutively. Said components may be administered in formulations comprising any combination of the substances.

Preferably, the method referred to in the tenth aspect comprises administering AKG and liprotamase simultaneously, separately or consecutively. Also preferably, the method referred to in the tenth aspect comprises administering AKG and pancrelipase simultaneously, separately or consecutively.

All references are hereby incorporated in their entirety. The following examples are not to be construed as limiting. The term "comprising" is used inclusively i.e. in the sense of "including, but not limited to".

EXAMPLES

Example 1

Induction of Hippocampal Neurogenesis

After the course of treatment as specified under Materials and Methods, the animals were sacrificed and the brains were analysed histologically to quantitate hippocampal neurogenesis.

Nestin is a marker for immature neurons. Nestin positive cells were found in the hippocampal layer of the pyramidal neurons. The somas of hippocampal cells displayed strong nestin staining. In some cells long processes that seem to be dendrites extended into deeper layers of the hippocampus, and these processes were nestin positive as well. In all of the CA fields of the hippocampus (CA1-CA3) these cells were structurally similar to pyramidal cells. The structural similarities between nestin positive cells and neurons allow regarding this type of cells as newly generated neurons.

The results indicated that both AKG and ENZ increased hippocampal neurogenesis compared to age matched controls (="old") (see FIG. 1). Note in particular, that the combination of AKG+ENZ was even more effective and resulted in a synergistic increase in neurogenesis (AKG+ENZ group was statistically significantly different from both AKG and ENZ groups.) The level of neurogenesis obtained by the combination therapy brought the level of neurogenesis in the old animals to the level of the young animals.

Conclusion: treatment with AKG, ENZ or AKG+ENZ increase neurogenesis. The combination of AKG+ENZ has a synergistic effect.

Example 2

Improvement of Cognitive Function/Memory

During the course of the treatment, the animals were subjected to T-maze test measuring cognitive function and/or memory as specified under Materials and Methods.

Figure 2:
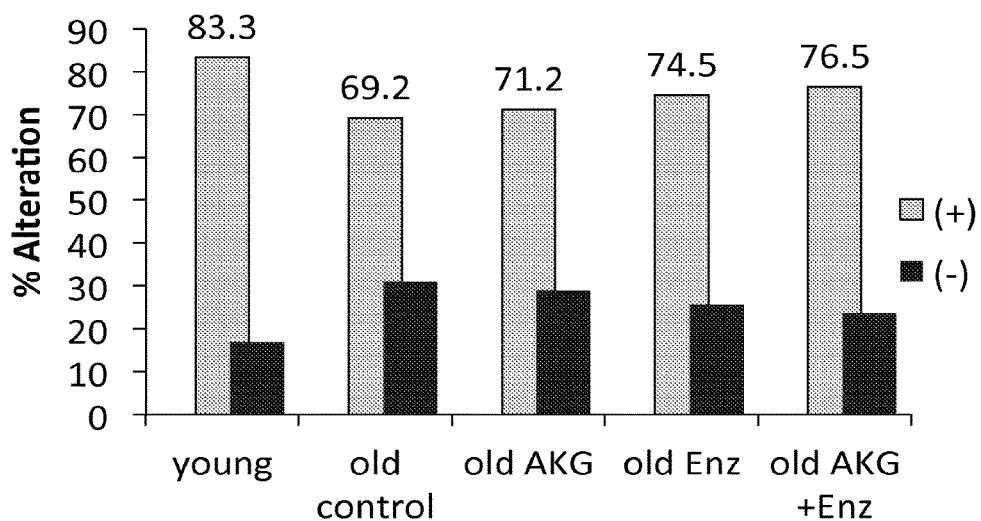
FIG. 2 illustrates improved cognitive performance by means of the present invention, detected in the percentage of spontaneous alterations in a T-maze test. (+) denotes correct trials—animal visited left and right arms, (−) denotes incorrect trials—animal visited the same arm twice.
Figure 3A:
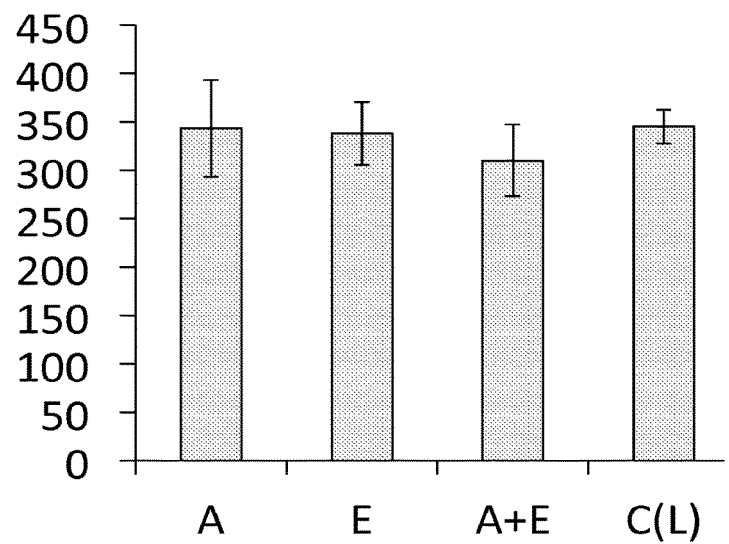
FIG. 3A: Platelets $10^3/\mu l$.
Figure 3B:
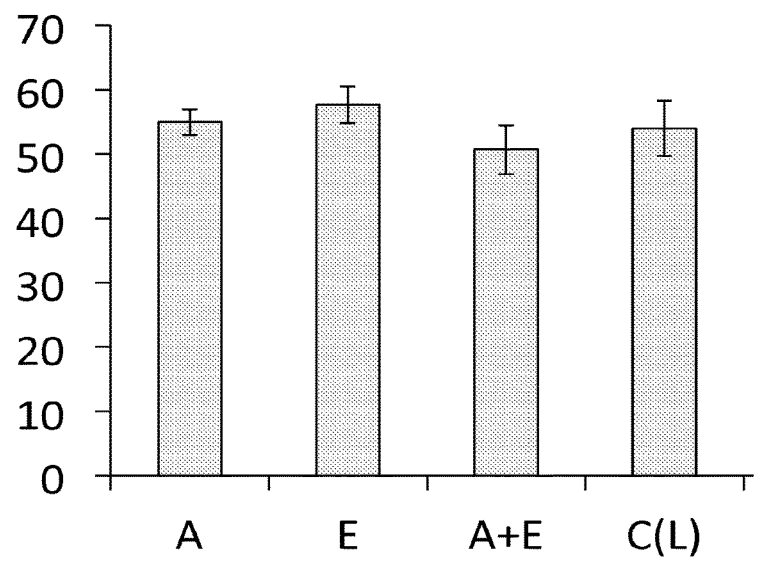
FIG. 3B: Lymphocyte (%).
Figure 3C:
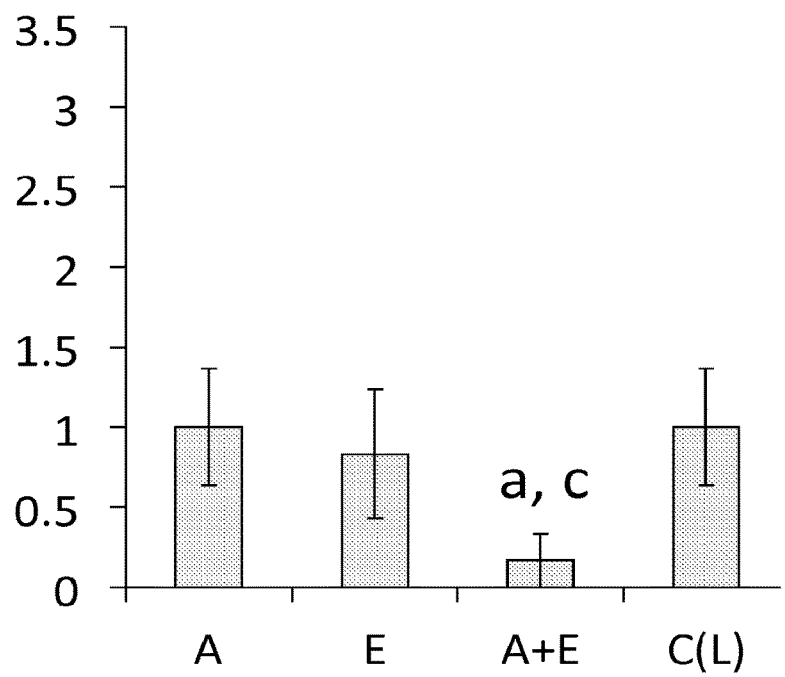
FIG. 3C: Eosinophils (%).
Figure 3D:
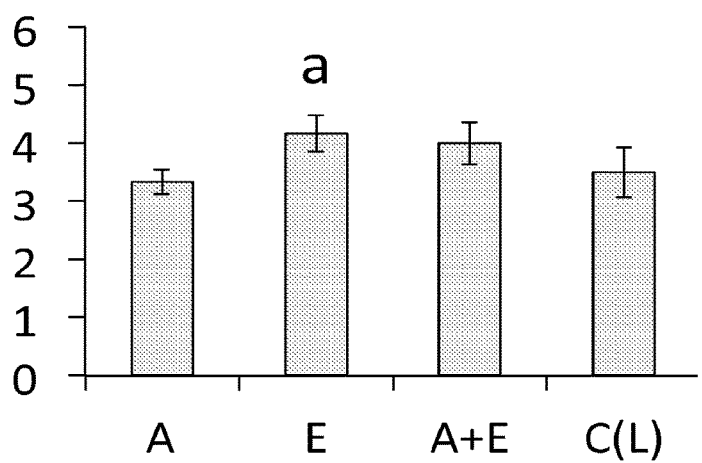
FIG. 3D: Monocytes (%). Letters a or c indicate statistically significant difference from control group ($p<0.05$).

Intriguingly, the results correlate perfectly with the increase in neurogenesis seen in Example 1 (see FIG. 2). This suggests that the neurogenesis resulted in improved cognitive function. Irrespective of the mechanism, the experiments shows that all of AKG, ENZ and AKG+ENZ improved cognition in old animals, with superior effect from the combination AKG+ENZ.

Example 3

Reduction in Eosinophils in Blood

Blood samples were analysed to determine effects in blood parameters as detailed under Materials and Methods.

Results (FIG. 3) showed that while platelet, lymphocyte and monocyte counts were unaffected by the treatments, the eosinophile count was markedly reduced by the combination of AKG+ENZ, but not by AKG by itself or ENZ by itself. Again, the combination of AKG+ENZ showed a synergistic effect.

Example 4

Synaptic Morphology Alterations

Introduction

We have chosen hippocampus as an object of our investigation because it is one of the major components of the brain of humans and other vertebrates. It belongs to the limbic system and plays important roles in the consolidation of information from short-term memory to long-term memory and spatial memory and navigation, emotion and behavior formation, cognitive function. Hippocampus is very vulnerable to different noxious stimuli. Damage to the hippocampus can result from oxygen starvation (hypoxia), encephalitis, medial temporal lobe epilepsy, age-related disorders (Alzheimer's disease) and others. Hippocampus is one of the first regions of the brain to suffer damage; memory loss and disorientation are included among the early symptoms.

It is worth to notice that hippocampal neurons are arranged in a specific spatial manner, which allows precise estimating of their quantity and quality.

Taken together, all these features (functional role, high vulnerability, neurons' arrangement) make hippocampus one of the most suitable systems for neurological research.

There are many diseases which are accompanied with loss of synapses. It is worth to notice that both amount and structure of synapses are impaired in diseases as Alzheimer's disease, stroke, Down syndrome, schizophrenia and traumatic brain injury and stress. Some authors have observed synaptic loss during normal aging.

Anatomic and functional studies indicate that there is decrease in the human brain volume and weight in individuals ≥60 yr old. It remains controversial whether the loss of brain volume represents neuronal loss, shrinkage, or both. Neuron loss does appear to occur in specific regions of the brain including the hippocampus, cerebral cortex, and amygdala.

The hippocampus is one of the brain regions that are prominently affected by neurodegeneration and functional decline even in what is still considered "normal aging". Decreased neuronal amount, a decrease in the number of synaptic connections, intracellular pathology, all these facts suggest that the hippocampal formation may be especially vulnerable to the effects of aging. Morphological studies of the hippocampus in young and old rats have revealed that pyramidal neurons in old rats are smaller and contain fewer dendritic branches and spines. The density of presynaptic terminals per length unit of postsynaptic membrane is also lower.

Each presynaptic terminal contains hundreds of synaptic vesicles filled with neurotransmitters. Synaptic vesicles are uniform organelles of 40 nm in diameter that constitute the central organelle for release and storage of a neurotransmitter that continuously undergoes an exo-endocytotic cycle. During this cycle vesicles change their positions within a presynaptic terminal and their number as well as spatial arrangement can provide insight into a neurotransmitter turnover.

When an action potential depolarizes the presynaptic plasma membrane, $Ca^{2+}$-channels open, and $Ca^{2+}$ flows into the terminal to trigger the exocytosis of synaptic vesicles, thereby releasing their neurotransmitters into the synaptic cleft.

The synaptic vesicle cycle consists of exocytosis followed by endocytosis and recycling. Synaptic vesicles are filled with neurotransmitters (NT) by active transport (neurotransmitter uptake) fueled by an electrochemical gradient established by a proton pump that acidifies the vesicle interior (vesicle acidification).

In preparation to synaptic exocytosis, synaptic vesicles are docked at the active zone, and primed by an ATP-dependent process that renders the vesicles competent to respond to a $Ca^{2+}$-signal. When an action potential depolarizes the presynaptic membrane, $Ca^{2+}$ channels open, causing a local increase in intracellular $Ca^{2+}$ at the active zone that triggers completion of the fusion reaction. Released neurotransmitters then bind to receptors associated with the postsynaptic density (PSD).

Results

In the middle portion of the CA1 stratum radiatum analyzed in the study, the great majority of synaptic inputs are excitatory and they preferentially terminate on the dendritic shaft, Taking into consideration these aspects, we could focus our analyses on the pool of excitatory CA1 spine synapses.

Figure 4:
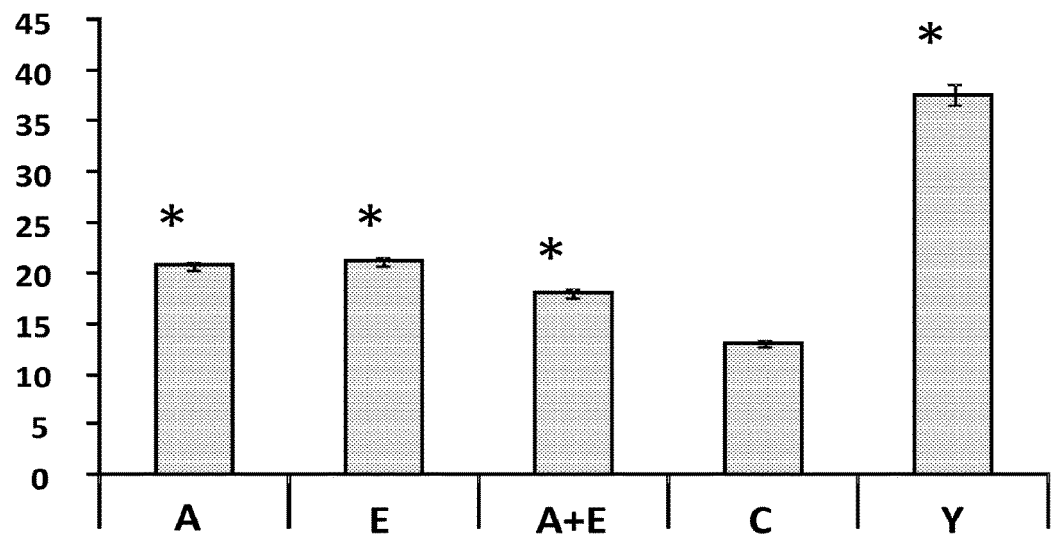
FIG. 4 shows average number of synaptic terminals per 100 $\mu m^2$ of hippocampal CA1 zone in different treatment groups. Asterisk (*) denotes statistical significance compared to the control group ($p<0.05$)
Figure 5:
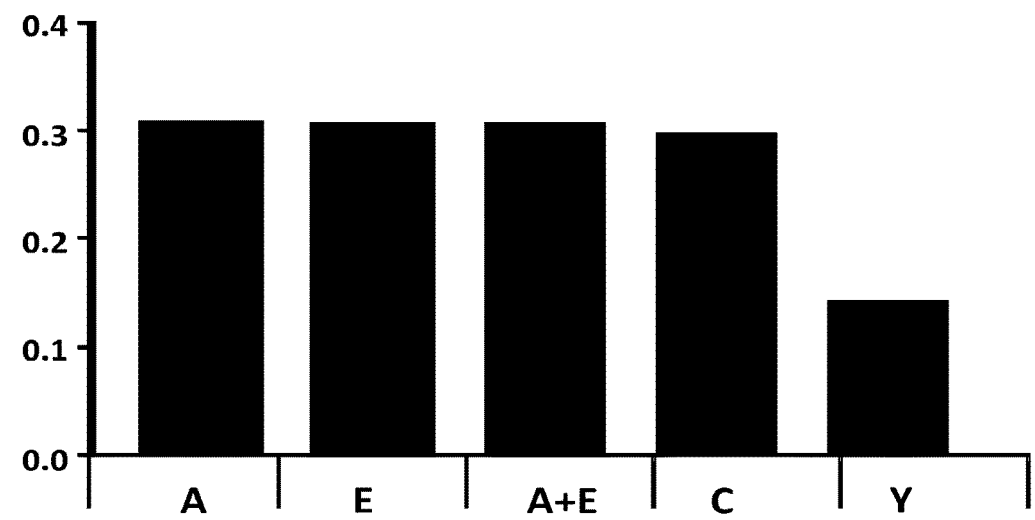
FIG. 5 shows average area ($\mu m^2$) of synaptic terminal in hippocampal CA1 zone in different treatment groups.
Figure 6A:
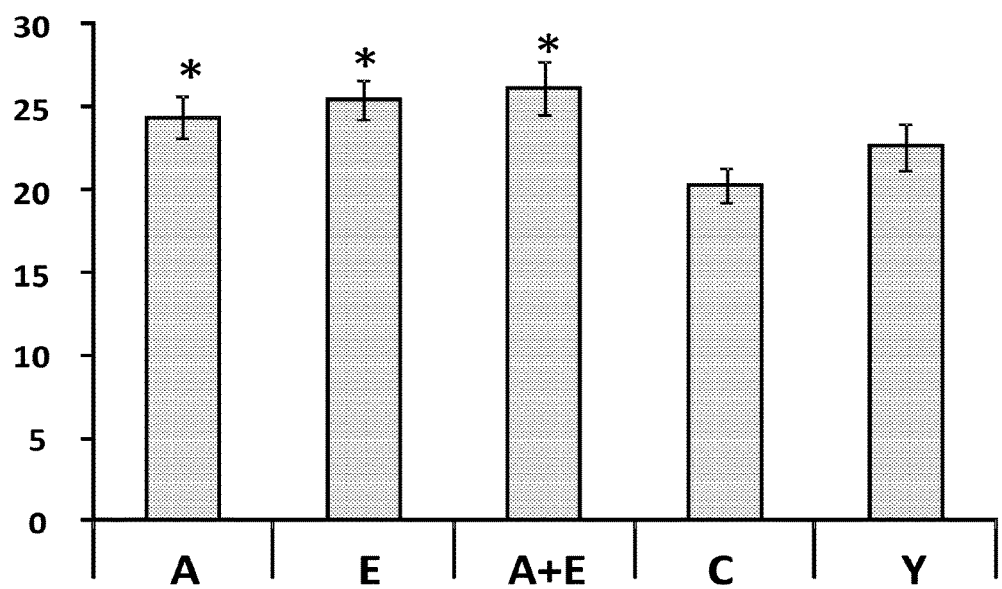
FIG. 6 shows average number of synaptic vesicles per synapse (A) and per 100 $\mu m^2$ of synaptic terminal (B) in hippocampal CA1 zone. Asterisk (*) denotes statistical significance compared to the control group ($p<0.05$).

The number of synaptic terminals per unit area (100 μm²) in old control animals is three times lower compared with young animals, but after long time treatment with AKG and/or lipase+protease+amylase the number of synaptic contacts increased to 55% (AKG and ENZ) and to 47% (AKG+ENZ) (FIG. 4). The area of synaptic terminals in old animals from all groups was three times greater than in young animals and was practically identical (FIG. 6).

Decrease in the number of SV per terminal in old animals compared with younger could also point at impairment of SV recycling process. It has been shown in many studies that synaptic vesicles proteins change their phosphorylation level under physiological and pathological conditions.

Figure 6B:
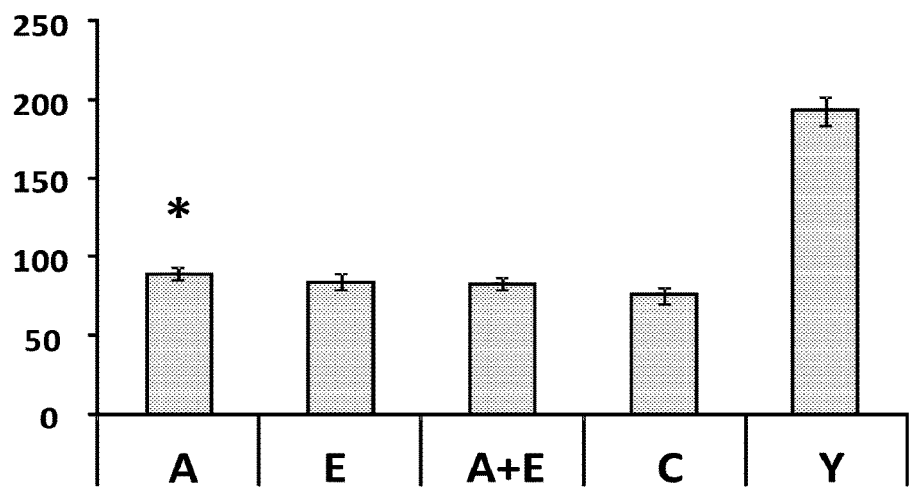

The number of SVs per presynaptic terminal was increased in AKG, ENZ and AKG+ENZ groups of gerbils compared to control old animals (FIG. 6A), while the number of SVs per square units (100 μm²) of terminal didn't differ from control, except for group 1 (FIG. 6B). This difference is due to the fact that the area of synaptic terminals in old animals from all groups was significantly greater than in young animals.

It is worth to notice that the group of young controls represents the physiological state of hippocampus, where synaptogenesis and synthesis of neurotransmitter is neither impaired with aging or some pathology, nor stimulated with any external factors. The number of vesicles in synapse tightly correlates with quantity of neurotransmitter, and this overshoot observed can be explained by stimulated by treatment-induced synthesis of neurotransmitter.

Figure 7:
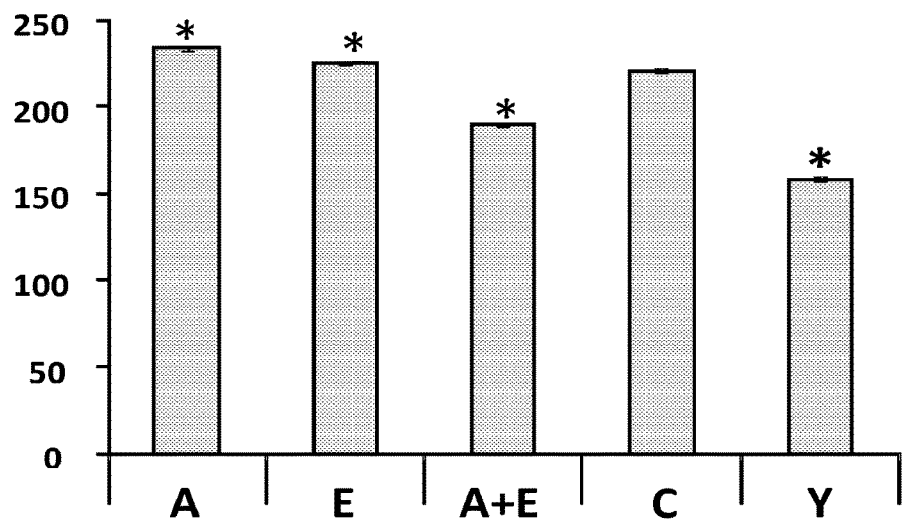
FIG. 7 shows average distance (nm) from synaptic vesicles to the active zone of presynaptic terminal. Asterisk (*) denotes statistical significance compared to the control group ($p<0.05$).

In the hippocampal synapses of the control old gerbils and of gerbils from groups 1 (AKG) and 2 (Enzymes) changes in spatial distribution of synaptic vesicles including the increase of a distance from a vesicle to the active zone were revealed (FIG. 7). These parameters are significantly lower in gerbils from 3 group (AKG+Enzymes) and are only slightly larger compared to those of young animals. There is a differentiation of synaptic vesicles' pools in dependence of their distance to active zone. The nearest pool of vesicles is designed to immediate release from pre-synaptic terminal and the fastest neurotransmission. Thereby, the reduction of average distance from synaptic vesicle to active zone is the sign of synaptic transmission improvement.

Figure 8:
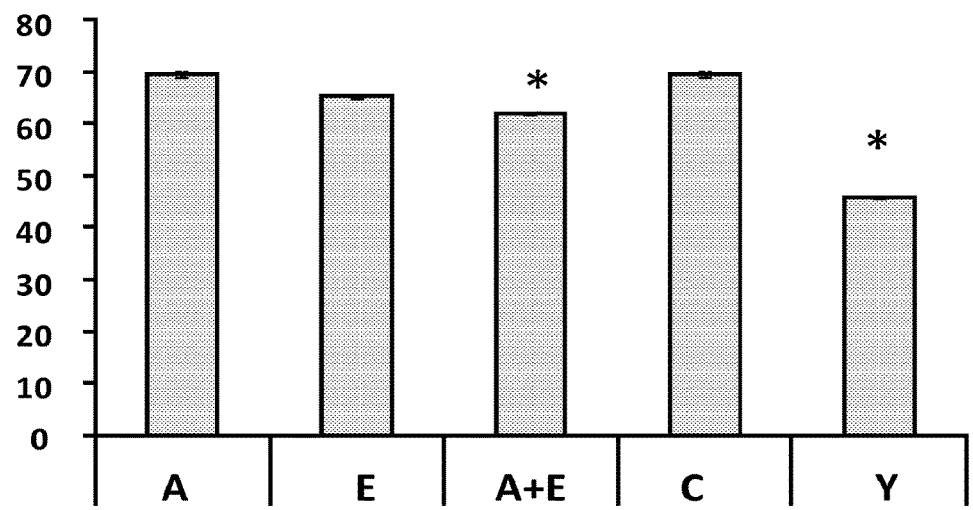
FIG. 8 shows average distance (nm) from vesicle to the to the nearest neighbor vesicle of presynaptic terminal. Asterisk (*) denotes statistical significance compared to the control group ($p<0.05$).

The analysis of vesicle clustering showed that SVs were also separated by larger distance: the average NND value estimated for control old animals was around 30% higher than for young (FIG. 8). Only for the 3 group it was revealed significant decrease of NND compared with control old animals (group 4). Distance to the 1st nearest neighbor of each vesicle was used to measure the tendency of synaptic vesicles to form spatial clusters. Note that vesicle density is number of vesicles per 1 unit area, and the NND parameter is not the average vesicle-to-vesicle distance, but the average distance to the nearest neighbor vesicle, the comparison of these parameters describes the difference of spatial distribution of vesicles in synapse.

Figure 9:
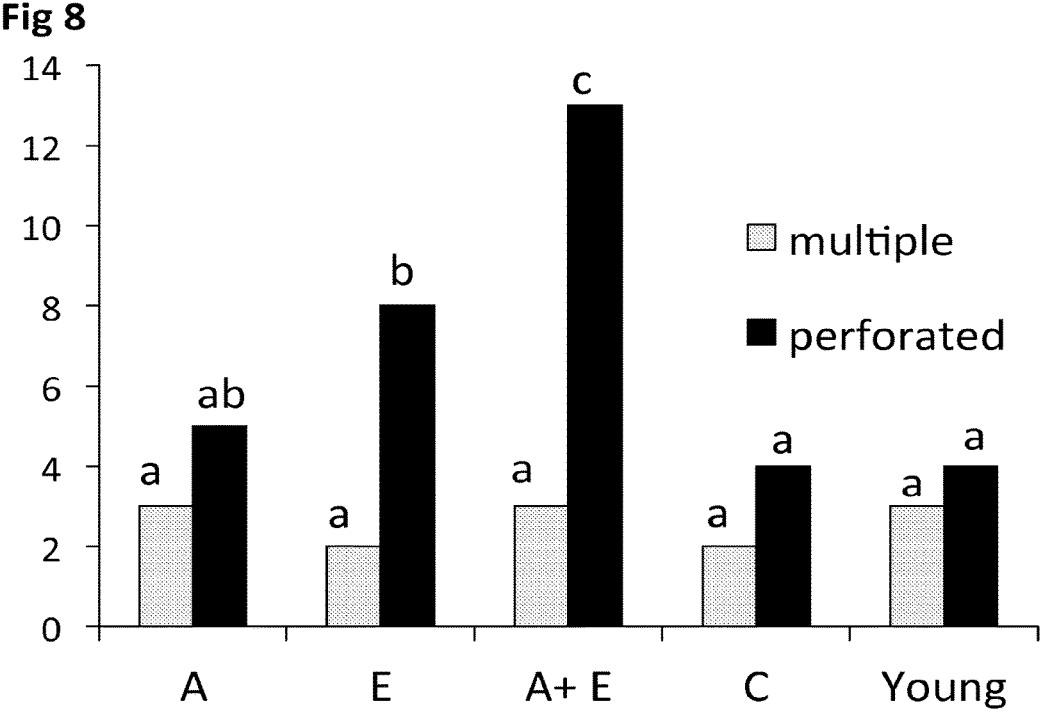
FIG. 9 shows proportion (%) of perforated and multiple synapses in hippocampal CA1 zone. The remainder represents simple synapses. The letter on the gray and black bars describe statistic difference when $p<0.05$. Columns with same letter are not statistically significantly different from each other. C denotes age-matched (old) control.

The long term treatments caused pronounced structural modifications of the types of synaptic terminals. An important increase in the perforated synapses amount in group 3 and 2, and in less degree, multiple spine boutons (FIG. 9) was observed.

Increase in the proportion of perforated synapses is thought to be more efficient in synaptic transmission and can be considered as compensatory mechanism in case of synaptic loss. Perforations have also been correlated with reactive synaptogenesis. Density of perforated synapses is coupled with recognition memory accuracy. Synapse remodeling is known as sign of neurological improvement, whereby the result is supportive for treatment and prophylaxis of neurological disorders in general and Alzheimer's in particular with the effective treatments.

The present study indicates that morphological alteration of synapses associated with synaptic plasticity might in fact relate to mechanisms of activation under altered physiological and pathological conditions. The parameters of synaptic contacts such as its dimensions, shape, size of presynaptic terminal, SV density and distribution, are all related to the efficacy of the synaptic transmission.

In summary, we describe here a number of morphological alterations within synaptic networks that are consequences of aging. We found that synaptic contacts are able to manifest modifications under inventive treatment conditions in animals. The decreased density of excitatory synapses in CA1 stratum radiatum of old animals compared with young ones is a sign of recovery after long-term treatment. Potentially deleterious morphological changes in the synapses, such as swelling of synaptic elements, depletion and rearrangement of SV pools, are accompanied by some apparently counter-balancing adaptive modifications: increase in perforations, which presumably could reflect strengthening of synaptic contacts, as well as relative increase in multiple spine boutons, which suggests reactive synaptogenesis.

Conclusions

In the hippocampal synapses of the old gerbils there are changes in spatial distribution of synaptic vesicles including the increase of a distance from a vesicle to the active zone and to the nearest neighbour vesicle.

Redistribution of different types of synaptic terminals takes place with the increase in perforated and multiple synapse numbers.

It is possible that these treatment-induced plastic changes might play a role in the mechanism of improvement of hippocampal neuronal function demonstrated in T-maze.

Example 5

Improved Cognitive Function

A repeat study using aged Mongolian Gerbils in the lines of Example 1 was undertaken, with modification of the enzyme components as specified in Materials and Methods.

Figure 10:
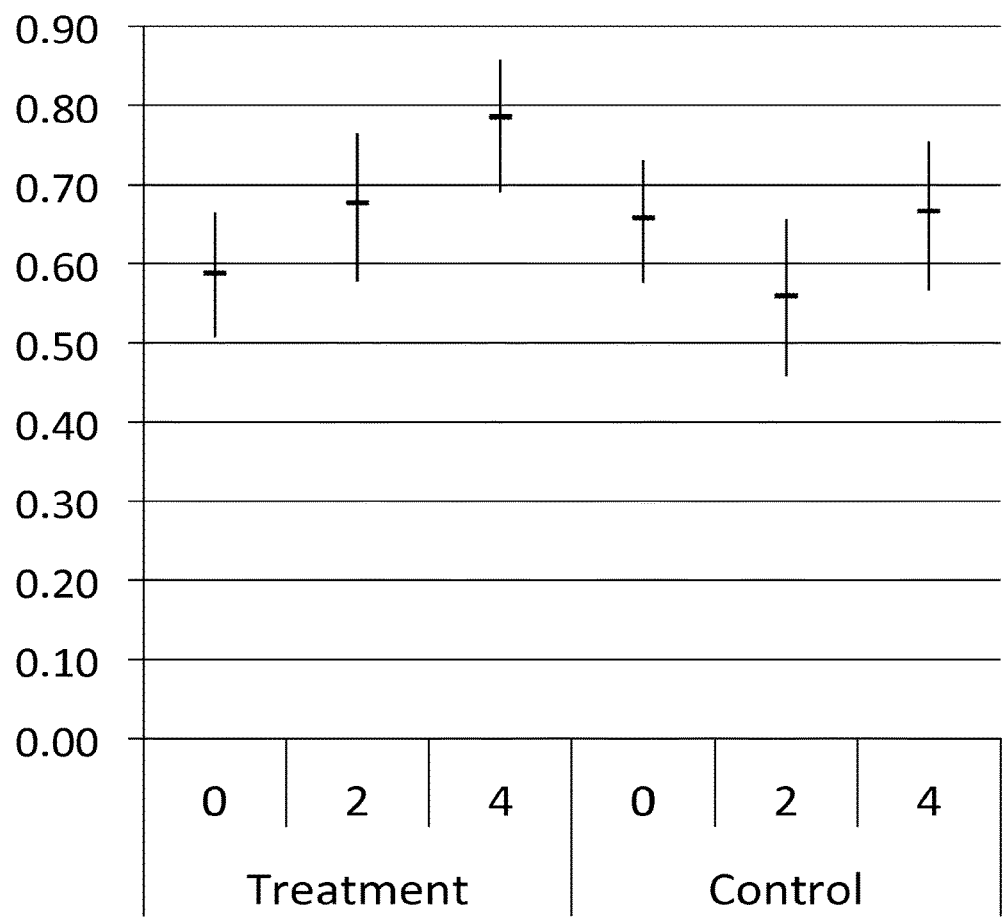
FIG. 10 illustrates improved cognitive performance by means of the present invention, detected in the percentage of spontaneous alterations in a T-maze test (See Example 5). The test was performed at start (0 months) and repeated at 2 and 4 months. The fraction of correct trials is shown, with 95% confidence interval calculated by modified Wald method. The treatment at baseline (0) and treatment at 4 months are statistically significantly different at least at $p<0.05$, since the 95% confidence intervals do not overlap.

In this experiment, there were two groups, control and treatment with AKG+enzymes. Behavioral analysis with T-maze was performed at 0, 2 and 4 months. As shown in FIG. 10, the treatment group improved its performance already at 2 months, with further significant improvement at 4 months, while there was no clear trend for the control group.

The results demonstrate that the results in Example 1 were repeatable with different enzyme preparations and concentrations, that a discernible effect was beginning to show at 2 months of treatment and improvement continued further during 4 months of treatment.

Figure 11:
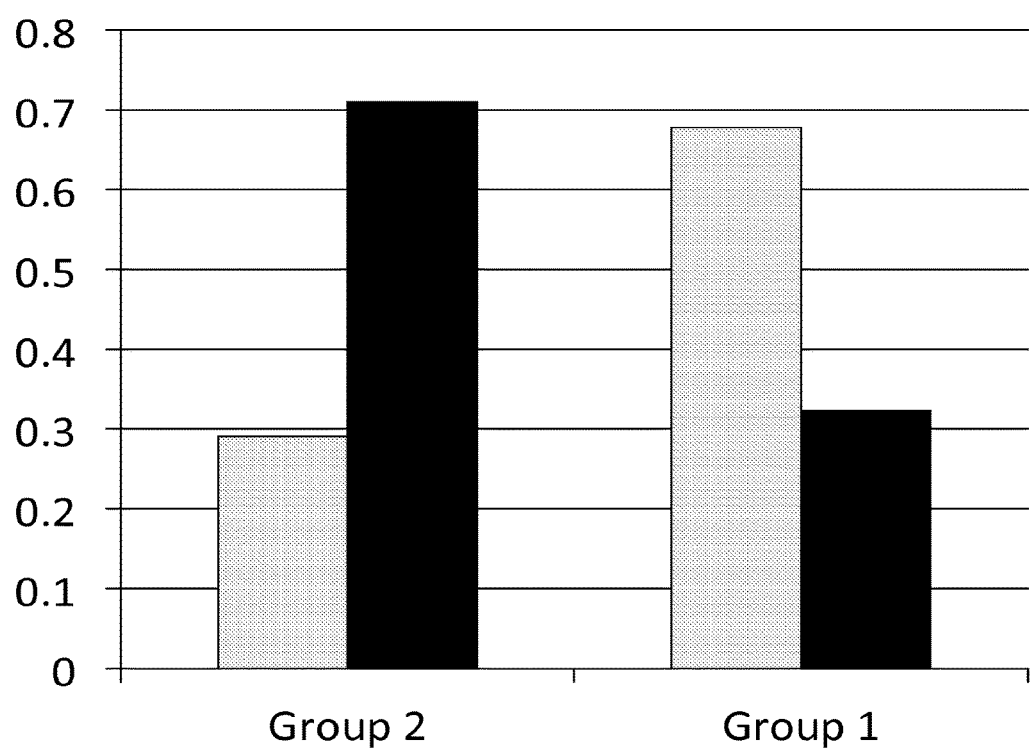
FIG. 11 shows the fraction of individual animals of Example 5 showing deteriorated or improved performance in the T-maze test at 2 and 4 months (results pooled) compared to their individual baseline performance. The fraction of animals in the group with improved performance is shown by the black columns, and the fraction with deteriorated performance is shown by the grey columns. Group 1=age-matched untreated controls, Group 2=treatment with AKG+enzymes. The difference is significant at $p<0.05$.

Statistics was calculated for each animal, both in the control and experimental groups. The difference between the percentage of tasks solved in the first trial and the mean of the percentages of tasks solved in two consequent trials was compared (FIG. 11). The individual animals in the experimental group (group 1) tend to demonstrate an increase of the number of solved tasks per test more often and, in cases where increase is seen, to have greater increases than the animals in the control group. The gerbils in the first group in 67.7% of cases demonstrate improved performance at 2 and 4 months (pooled results) compared to performance compared to performance at baseline. In contrast, only 29% in the control group (Group 2) showed improved performance (FIG. 11).

In conclusion animals without any treatment tend to show worse results over time (possibly due to aging) but treatment animals tend to show improved performance over time, demonstrating a cognitive performance-enhancing effect of the treatment.

The measure allows discrimination of if there are individual shifts in the ability to pass the test over the course of treatment. Since the number of animals is large enough, the U-statistic, the deciding statistic of the Mann-Whitney test, is approximately Gaussian with known parameters, and the probability that either group is described with the same probabilistic law is less than 0.05, which proves that with the confidence level of 0.05 there are qualitative differences between two groups.

Materials and Methods

In Example 1. the animals were fed Labofeed B standard chow (from Labofeed company; Andrzej Morawski Feed Production Plant, Kcynia near. Bydgoszcz, Poland) supplemented with test compounds as specified in table 1.

TABLE 1

Treatment groups, example 1

| Group | Additive |
|---|---|
| Age-matched controls (also denoted C, Contr (old), old controlor C(L)) | None |
| AKG (also denoted A or old AKG) | 1% calcium AKG by weight<br>1% sodium AKG by weight<br>Total AKG approx. 114 mmol/kg |
| ENZ (also denoted E, Enz or old Enz) | lipase 600000 USP units/kg<br>protease 400000 USP units/kg<br>amylase 60000 USP units/kg |

TABLE 1-continued

Treatment groups, example 1

| Group | Additive |
|---|---|
| AKG + ENZ (also denoted A + E, AKG − Enz, old AKG + Enz) | 1% calcium AKG by weight<br>1% sodium AKG by weight<br>lipase 600000 USP units/kg<br>protease 400000 USP units/kg<br>amylase 60000 USP units/kg |
| Young controls (also denoted Y, Contr (young), Young) | None |

The lipase, protease and amylase were obtained as capsules containing 30,000 USP units/capsule of lipase, 20,000 USP units/capsule of protease, and 3,000 USP units/capsule of amylase) prepared as shown in Table 2. Contents of 20 capsules were mixed per each kg of feed for the ENZ and AKG+ENZ groups.

TABLE 2

Capsules with lipase, protease and amylase

| Component | Amount (USP units/capsule) | Amount (mg/capsule) | Supplier | Cat no |
|---|---|---|---|---|
| Burkholderia cepacia lipase | 30,000 | 13.1 | Sigma Aldrich | 534641 |
| Aspergillus melleus proteinase | 20,000 | 14.3 | Sigma Aldrich | P4032 |
| Aspergillus oryzae α-amylase | 3,000 | 30.0 | Sigma Aldrich | 10065 |

The capsules also contained filler up to a weight of 200 mg.

In Example 5, the animals were fed Labofeed B standard chow (from Labofeed company; Andrzej Morawski Feed Production Plant, Kcynia near. Bydgoszcz, Poland) supplemented with test compounds as specified in table 3.

TABLE 3

Treatment groups, Example 5

| Group | Additive |
|---|---|
| Age-matched controls | None |
| AKG + ENZ (also denoted A + E) | 1% calcium AKG by weight<br>1% sodium AKG by weight<br>Total AKG ca. 114 mmol/kg<br>lipase 200000 USP units/kg<br>protease 750000 USP units/kg<br>amylase 664000 USP units/kg |

The enzymes in table 3 are further specified in Table 4.

TABLE 4

Specification of lipase, protease and amylase in Example 5

| Component | Determined activity USP/mg | Amount (mg/kg fodder) | Supplier | Manufacturer designation |
|---|---|---|---|---|
| Burkholderia cepacia lipase | 400 | 500 | Amano | Lipase PS "Amano" SD |
| Aspergillus melleus proteinase | 1500 | 500 | Amano | Protease DS-K |
| Aspergillus oryzae α-amylase | 3370 | 16850 | Amano | Amylase DS |

Study Outline
Animals and Animal Care (Example 1-4)

For long-lasting feeding (during 6 month) 75 old male Mongolian gerbils, randomly selected, were used. Those selected were approximately 1.5 years of age at start of the experiment with the mean body weight of 88.0±6 g and 2 years of age at experiment finish. Additionally, 6 male gerbils of "young"-adult (6 month) of age were used for additional "age-control" (denoted "Control(young)", or "Young" or "Y" in the graphs).

The gerbils were housed in individual cages and divided into groups receiving different treatments (Table 1). Each cage was equipped with a drinking bottle.

Gerbils (4-8 per cage) were housed in clear polycarbonate cages (48×27×20 cm) containing corn-cob bedding, paper towels for nesting material, and a tin can (13 cm long×10 cm diameter) for enrichment.

Food (individual for each group, Tables 1-2) and water were available ad lib, and provided once per day.

Lights were on from 07.00 to 19.00 h, and room temperature and humidity were maintained at approximately 23° C. and 30-70%, respectively.

All gerbils were acclimated to cages for a week before the start of the experiment.

Animals and Animal Care (Example 5)

Animal care was similar to Examples 1-4 above with the exception that only two groups were included and treated in accordance with Tables 3-4.

Control groups comprised 15 animals whereas the age-matched treatment group comprised 16 animals.

Assessment of Hippocampal Neurogenesis
Preparing of Morphological Samples

At the end of the experiment, the gerbils were anaesthetized with ketamine (100 mg/kg body weight i/m) and fixed by transcardial perfusion with 4% formaldehyde and 0.25% glutaraldehyde in 0.1M phosphate buffer. After perfusion the brains were isolated and separated for two hemispheres.

Immunocytochemistry

Samplings for immunohistochemistry (one hemisphere of each animal) were postfixed overnight in the same fixative at +4° C. The next day they were cut in 50-µm-thick frontal slices by a vibratome Vibroslice 752M (Campden Instruments Ltd, Great Britain). Brain slices were washed out with 0.1M phosphate buffer pH 7.4 and treated in blocking solution containing 1% normal goat serum and 0.3% Triton X-100. Goat monoclonal anti-nestin antibodies (1:500) (Santa Cruz biotechnology, inc, USA) were used for detection proliferating immature neuronal cells, which express the neural specific intermediate filament nestin. Slices were incubated with primary antibodies during 16 hours at +4° C. After washing slices were incubated with anti-goat secondary antibodies conjugated with Alexa Fluor 647 (1:1000) (Molecular probes, USA) for 1.5 h at room temperature. Then slices were washed out, placed on histological slides and mounted with Fluorescence Mounting Media (Dako, Denmark). Images of hippocampal tissue were taken by confocal FV1000-BX61WI microscope (Olympus, Japan). Qualitative analysis of nestin-positive cells distribution in CA1 hippocampal area was realized for each experimental group.

Statistical Analysis

All the statistical data were estimated with STATISTICA ver.7.0 (StatSoft, USA). The two-tailed Kolmogorov-Smirnov test was used to assess the differences between samples (p<0.05 was considered to indicate statistical significance). SE (standard error) was used as error bars.

Synaptic Alterations
Electron Microscopy

Gerbils were anaesthetized with sublethal dose of ketamine (100 mg/kg body weight i/m) and fixed by transcardial perfusion with 4% formaldehyde and 0.25% glutaraldehyde in 0.1M phosphate buffer. After perfusion the brains were isolated and separated on two hemispheres.

One hemisphere of each animal was used for immunohistochemical assay.

The hippocampus from another hemisphere of each animal was isolated and cut in 400-µm-thick transverse slices by a chopper (McIlwain tissue chopper, Great Britain). Slices were postfixed in fixative solution with 2.5% of glutaraldehyde for 1.5 h and then in 1% OsO4 for 1 h. Tissue slices were then dehydrated in an ascending series of ethanol followed by dry acetone and embedded in EPON resin according to official protocol. The sections were produced by ultramicrotome LKB-8800. Toluidine blue-stained semi-thin (1 µm) sections of hippocampus were used to localize hippocampal CA1 area. For electron microscopy, ultra-thin sections (70 nm) from the middle portion of CA1 stratum pyramidale and stratum radiatum were stained with uranyl acetate and lead citrate.

The images were taken with JEM-100CX (Jeol, Japan) transmission electron microscope at magnification of ×10 000. Calculations were provided for three animals from each group:

Group 1 (AKG)
Group 2 (Lipase+protease+amylase)
Group 3 (AKG+Lipase+protease+amylase)
Group 4 (old control)
Group (Young)

The synaptic terminals of the investigated area revealed high degree of structural plasticity including modifications in the ratio of different forms of synaptic terminals (simple, perforated, multiple boutons). Perforated synapse was defined as a synapse with discontinuous PSD. The synapses with more than one spine contacting the same presynaptic terminal were classified as multiple spine boutons (MSB).

For the analysis of SV's distribution, x- and y-coordinates of SV profile centers and points tracing the active zone of a synapse were marked with UTHSCSA ImageTool software (version 3, University of Texas, San Antonio, Tex.; ftp://maxrad6.uthscsa.edu) on digitized micrographs, using the point tool. The shortest distance from a SV to the active zone profile (hence forth referred to as an active zone distance (AZD), as well as spatial proximity of SV profiles to each other (referred to as the nearest neighbor distance (NND)) were quantified using the nearest neighbor formalism with LoClust software as described (Nikonenko and Skibo, 2004).

AZD and NND quantities were pooled together per group. For each experimental and control condition, 100 synapses containing SVs have been analyzed. Statistical analysis was performed using Statistica software (version 5, StatSoft, USA). Values are shown as mean±standard error of the mean (SEM). The two-tailed Kolmogorov-Smirnov test was used to assess the differences between samples (P<0.05 was considered to indicate statistical significance).

Synaptic Morphometry and Quantification of Synaptic Vesicles' Distribution

Estimations of synapse density were carried out on single photos by counting all asymmetric spine synapses (determined by the presence of a spine head with prominent PSD and docked synaptic vesicles (SV) in the active zone of a presynaptic terminal) on the micrograph surface limited by the counting frame (36 mkm² test area) followed by calculation of the number of synapses per surface unit area.

Behavioural Tests

T Maze Spontaneous Alternation

T Maze Spontaneous Alternation is a behavioral test for measuring exploratory behavior in animals, especially rodent models for CNS disorders. This test is based on the willingness of rodents to explore a new environment, i.e. they prefer to visit a new arm of the maze rather than a familiar arm. Many parts of the brain—including the hippocampus, septum, basal forebrain, and prefrontal cortex—are involved in this task.

This protocol details a method for using a T-maze to assess the cognitive ability of rodents. The T-maze is an elevated or enclosed apparatus in the form of a T placed horizontally. Animals are started from the base of the T and allowed to choose one of the goal arms abutting the other end of the stem. If two trials are given in quick succession, on the second trial the rodent tends to choose the arm not visited before, reflecting memory of the first choice. This is called 'spontaneous alternation'. Both spontaneous and rewarded alternation are very sensitive to dysfunction of the hippocampus, but other brain structures are also involved. Each trial should be completed in less than 2 min, but the total number of trials required will vary according to statistical and scientific requirements. Alternation reflects the motivation of the animal to explore its environment and locate the presence of resources such as food, water, mates or shelter. Animals do not need to be deprived of such resources to show alternation behavior; in this case it is called 'spontaneous alternation'.

Subjects were first placed in the start arm of the T Maze. Upon leaving the start arm, subjects chose between entering either the left or the right goal arm. With repeated trials, the animals showed less of a tendency to enter a previously visited arm. The percentage of alternation (number of turns in each goal arm) and total trial duration were recorded.

In Example 2, the animals were subjected to the test once.

In Example 5, the animals were subjected to the test on 4 consecutive days at the start of the experiment, and subsequently subjected to the test on 3 consecutive days after 2 months and 4 months of treatment.

Blood Biochemistry

At the end of the study, hematological parameters were studied using hematolyzer ABX Micros 60 OT (France) according standard methods.

TABLE X

| # | A | B | C |
|---|---|---|---|
| 1 | 1 | 1 | 1 |
| 2 | 1 | 1 | 2 |
| 3 | 1 | 1 | 3 |
| 4 | 1 | 1 | 4 |
| 5 | 1 | 1 | 5 |
| 6 | 1 | 1 | 6 |
| 7 | 1 | 1 | 7 |
| 8 | 1 | 1 | 8 |
| 9 | 1 | 1 | 9 |
| 10 | 1 | 1 | 10 |
| 11 | 1 | 2 | 1 |
| 12 | 1 | 2 | 2 |
| 13 | 1 | 2 | 3 |
| 14 | 1 | 2 | 4 |
| 15 | 1 | 2 | 5 |
| 16 | 1 | 2 | 6 |
| 17 | 1 | 2 | 7 |
| 18 | 1 | 2 | 8 |
| 19 | 1 | 2 | 9 |
| 20 | 1 | 2 | 10 |
| 21 | 1 | 3 | 1 |
| 22 | 1 | 3 | 2 |
| 23 | 1 | 3 | 3 |
| 24 | 1 | 3 | 4 |
| 25 | 1 | 3 | 5 |
| 26 | 1 | 3 | 6 |
| 27 | 1 | 3 | 7 |
| 28 | 1 | 3 | 8 |
| 29 | 1 | 3 | 9 |
| 30 | 1 | 3 | 10 |
| 31 | 1 | 4 | 1 |
| 32 | 1 | 4 | 2 |
| 33 | 1 | 4 | 3 |
| 34 | 1 | 4 | 4 |
| 35 | 1 | 4 | 5 |
| 36 | 1 | 4 | 6 |
| 37 | 1 | 4 | 7 |
| 38 | 1 | 4 | 8 |
| 39 | 1 | 4 | 9 |
| 40 | 1 | 4 | 10 |
| 41 | 1 | 5 | 1 |
| 42 | 1 | 5 | 2 |
| 43 | 1 | 5 | 3 |
| 44 | 1 | 5 | 4 |
| 45 | 1 | 5 | 5 |
| 46 | 1 | 5 | 6 |
| 47 | 1 | 5 | 7 |
| 48 | 1 | 5 | 8 |
| 49 | 1 | 5 | 9 |
| 50 | 1 | 5 | 10 |
| 51 | 1 | 6 | 1 |
| 52 | 1 | 6 | 2 |
| 53 | 1 | 6 | 3 |
| 54 | 1 | 6 | 4 |
| 55 | 1 | 6 | 5 |
| 56 | 1 | 6 | 6 |
| 57 | 1 | 6 | 7 |
| 58 | 1 | 6 | 8 |
| 59 | 1 | 6 | 9 |
| 60 | 1 | 6 | 10 |
| 61 | 1 | 7 | 1 |
| 62 | 1 | 7 | 2 |
| 63 | 1 | 7 | 3 |
| 64 | 1 | 7 | 4 |
| 65 | 1 | 7 | 5 |
| 66 | 1 | 7 | 6 |
| 67 | 1 | 7 | 7 |
| 68 | 1 | 7 | 8 |
| 69 | 1 | 7 | 9 |
| 70 | 1 | 7 | 10 |
| 71 | 1 | 8 | 1 |
| 72 | 1 | 8 | 2 |
| 73 | 1 | 8 | 3 |
| 74 | 1 | 8 | 4 |
| 75 | 1 | 8 | 5 |
| 76 | 1 | 8 | 6 |
| 77 | 1 | 8 | 7 |
| 78 | 1 | 8 | 8 |
| 79 | 1 | 8 | 9 |
| 80 | 1 | 8 | 10 |
| 81 | 1 | 9 | 1 |
| 82 | 1 | 9 | 2 |
| 83 | 1 | 9 | 3 |
| 84 | 1 | 9 | 4 |
| 85 | 1 | 9 | 5 |
| 86 | 1 | 9 | 6 |
| 87 | 1 | 9 | 7 |
| 88 | 1 | 9 | 8 |
| 89 | 1 | 9 | 9 |
| 90 | 1 | 9 | 10 |
| 91 | 1 | 10 | 1 |
| 92 | 1 | 10 | 2 |
| 93 | 1 | 10 | 3 |
| 94 | 1 | 10 | 4 |
| 95 | 1 | 10 | 5 |
| 96 | 1 | 10 | 6 |
| 97 | 1 | 10 | 7 |

TABLE X-continued

| # | A | B | C |
|---|---|---|---|
| 98 | 1 | 10 | 8 |
| 99 | 1 | 10 | 9 |
| 100 | 1 | 10 | 10 |
| 101 | 2 | 1 | 1 |
| 102 | 2 | 1 | 2 |
| 103 | 2 | 1 | 3 |
| 104 | 2 | 1 | 4 |
| 105 | 2 | 1 | 5 |
| 106 | 2 | 1 | 6 |
| 107 | 2 | 1 | 7 |
| 108 | 2 | 1 | 8 |
| 109 | 2 | 1 | 9 |
| 110 | 2 | 1 | 10 |
| 111 | 2 | 2 | 1 |
| 112 | 2 | 2 | 2 |
| 113 | 2 | 2 | 3 |
| 114 | 2 | 2 | 4 |
| 115 | 2 | 2 | 5 |
| 116 | 2 | 2 | 6 |
| 117 | 2 | 2 | 7 |
| 118 | 2 | 2 | 8 |
| 119 | 2 | 2 | 9 |
| 120 | 2 | 2 | 10 |
| 121 | 2 | 3 | 1 |
| 122 | 2 | 3 | 2 |
| 123 | 2 | 3 | 3 |
| 124 | 2 | 3 | 4 |
| 125 | 2 | 3 | 5 |
| 126 | 2 | 3 | 6 |
| 127 | 2 | 3 | 7 |
| 128 | 2 | 3 | 8 |
| 129 | 2 | 3 | 9 |
| 130 | 2 | 3 | 10 |
| 131 | 2 | 4 | 1 |
| 132 | 2 | 4 | 2 |
| 133 | 2 | 4 | 3 |
| 134 | 2 | 4 | 4 |
| 135 | 2 | 4 | 5 |
| 136 | 2 | 4 | 6 |
| 137 | 2 | 4 | 7 |
| 138 | 2 | 4 | 8 |
| 139 | 2 | 4 | 9 |
| 140 | 2 | 4 | 10 |
| 141 | 2 | 5 | 1 |
| 142 | 2 | 5 | 2 |
| 143 | 2 | 5 | 3 |
| 144 | 2 | 5 | 4 |
| 145 | 2 | 5 | 5 |
| 146 | 2 | 5 | 6 |
| 147 | 2 | 5 | 7 |
| 148 | 2 | 5 | 8 |
| 149 | 2 | 5 | 9 |
| 150 | 2 | 5 | 10 |
| 151 | 2 | 6 | 1 |
| 152 | 2 | 6 | 2 |
| 153 | 2 | 6 | 3 |
| 154 | 2 | 6 | 4 |
| 155 | 2 | 6 | 5 |
| 156 | 2 | 6 | 6 |
| 157 | 2 | 6 | 7 |
| 158 | 2 | 6 | 8 |
| 159 | 2 | 6 | 9 |
| 160 | 2 | 6 | 10 |
| 161 | 2 | 7 | 1 |
| 162 | 2 | 7 | 2 |
| 163 | 2 | 7 | 3 |
| 164 | 2 | 7 | 4 |
| 165 | 2 | 7 | 5 |
| 166 | 2 | 7 | 6 |
| 167 | 2 | 7 | 7 |
| 168 | 2 | 7 | 8 |
| 169 | 2 | 7 | 9 |
| 170 | 2 | 7 | 10 |
| 171 | 2 | 8 | 1 |
| 172 | 2 | 8 | 2 |
| 173 | 2 | 8 | 3 |
| 174 | 2 | 8 | 4 |
| 175 | 2 | 8 | 5 |
| 176 | 2 | 8 | 6 |
| 177 | 2 | 8 | 7 |
| 178 | 2 | 8 | 8 |
| 179 | 2 | 8 | 9 |
| 180 | 2 | 8 | 10 |
| 181 | 2 | 9 | 1 |
| 182 | 2 | 9 | 2 |
| 183 | 2 | 9 | 3 |
| 184 | 2 | 9 | 4 |
| 185 | 2 | 9 | 5 |
| 186 | 2 | 9 | 6 |
| 187 | 2 | 9 | 7 |
| 188 | 2 | 9 | 8 |
| 189 | 2 | 9 | 9 |
| 190 | 2 | 9 | 10 |
| 191 | 2 | 10 | 1 |
| 192 | 2 | 10 | 2 |
| 193 | 2 | 10 | 3 |
| 194 | 2 | 10 | 4 |
| 195 | 2 | 10 | 5 |
| 196 | 2 | 10 | 6 |
| 197 | 2 | 10 | 7 |
| 198 | 2 | 10 | 8 |
| 199 | 2 | 10 | 9 |
| 200 | 2 | 10 | 10 |
| 201 | 3 | 1 | 1 |
| 202 | 3 | 1 | 2 |
| 203 | 3 | 1 | 3 |
| 204 | 3 | 1 | 4 |
| 205 | 3 | 1 | 5 |
| 206 | 3 | 1 | 6 |
| 207 | 3 | 1 | 7 |
| 208 | 3 | 1 | 8 |
| 209 | 3 | 1 | 9 |
| 210 | 3 | 1 | 10 |
| 211 | 3 | 2 | 1 |
| 212 | 3 | 2 | 2 |
| 213 | 3 | 2 | 3 |
| 214 | 3 | 2 | 4 |
| 215 | 3 | 2 | 5 |
| 216 | 3 | 2 | 6 |
| 217 | 3 | 2 | 7 |
| 218 | 3 | 2 | 8 |
| 219 | 3 | 2 | 9 |
| 220 | 3 | 2 | 10 |
| 221 | 3 | 3 | 1 |
| 222 | 3 | 3 | 2 |
| 223 | 3 | 3 | 3 |
| 224 | 3 | 3 | 4 |
| 225 | 3 | 3 | 5 |
| 226 | 3 | 3 | 6 |
| 227 | 3 | 3 | 7 |
| 228 | 3 | 3 | 8 |
| 229 | 3 | 3 | 9 |
| 230 | 3 | 3 | 10 |
| 231 | 3 | 4 | 1 |
| 232 | 3 | 4 | 2 |
| 233 | 3 | 4 | 3 |
| 234 | 3 | 4 | 4 |
| 235 | 3 | 4 | 5 |
| 236 | 3 | 4 | 6 |
| 237 | 3 | 4 | 7 |
| 238 | 3 | 4 | 8 |
| 239 | 3 | 4 | 9 |
| 240 | 3 | 4 | 10 |
| 241 | 3 | 5 | 1 |
| 242 | 3 | 5 | 2 |
| 243 | 3 | 5 | 3 |
| 244 | 3 | 5 | 4 |
| 245 | 3 | 5 | 5 |
| 246 | 3 | 5 | 6 |
| 247 | 3 | 5 | 7 |
| 248 | 3 | 5 | 8 |
| 249 | 3 | 5 | 9 |
| 250 | 3 | 5 | 10 |
| 251 | 3 | 6 | 1 |
| 252 | 3 | 6 | 2 |
| 253 | 3 | 6 | 3 |

TABLE X-continued

| # | A | B | C |
|---|---|---|---|
| 254 | 3 | 6 | 4 |
| 255 | 3 | 6 | 5 |
| 256 | 3 | 6 | 6 |
| 257 | 3 | 6 | 7 |
| 258 | 3 | 6 | 8 |
| 259 | 3 | 6 | 9 |
| 260 | 3 | 6 | 10 |
| 261 | 3 | 7 | 1 |
| 262 | 3 | 7 | 2 |
| 263 | 3 | 7 | 3 |
| 264 | 3 | 7 | 4 |
| 265 | 3 | 7 | 5 |
| 266 | 3 | 7 | 6 |
| 267 | 3 | 7 | 7 |
| 268 | 3 | 7 | 8 |
| 269 | 3 | 7 | 9 |
| 270 | 3 | 7 | 10 |
| 271 | 3 | 8 | 1 |
| 272 | 3 | 8 | 2 |
| 273 | 3 | 8 | 3 |
| 274 | 3 | 8 | 4 |
| 275 | 3 | 8 | 5 |
| 276 | 3 | 8 | 6 |
| 277 | 3 | 8 | 7 |
| 278 | 3 | 8 | 8 |
| 279 | 3 | 8 | 9 |
| 280 | 3 | 8 | 10 |
| 281 | 3 | 9 | 1 |
| 282 | 3 | 9 | 2 |
| 283 | 3 | 9 | 3 |
| 284 | 3 | 9 | 4 |
| 285 | 3 | 9 | 5 |
| 286 | 3 | 9 | 6 |
| 287 | 3 | 9 | 7 |
| 288 | 3 | 9 | 8 |
| 289 | 3 | 9 | 9 |
| 290 | 3 | 9 | 10 |
| 291 | 3 | 10 | 1 |
| 292 | 3 | 10 | 2 |
| 293 | 3 | 10 | 3 |
| 294 | 3 | 10 | 4 |
| 295 | 3 | 10 | 5 |
| 296 | 3 | 10 | 6 |
| 297 | 3 | 10 | 7 |
| 298 | 3 | 10 | 8 |
| 299 | 3 | 10 | 9 |
| 300 | 3 | 10 | 10 |
| 301 | 4 | 1 | 1 |
| 302 | 4 | 1 | 2 |
| 303 | 4 | 1 | 3 |
| 304 | 4 | 1 | 4 |
| 305 | 4 | 1 | 5 |
| 306 | 4 | 1 | 6 |
| 307 | 4 | 1 | 7 |
| 308 | 4 | 1 | 8 |
| 309 | 4 | 1 | 9 |
| 310 | 4 | 1 | 10 |
| 311 | 4 | 2 | 1 |
| 312 | 4 | 2 | 2 |
| 313 | 4 | 2 | 3 |
| 314 | 4 | 2 | 4 |
| 315 | 4 | 2 | 5 |
| 316 | 4 | 2 | 6 |
| 317 | 4 | 2 | 7 |
| 318 | 4 | 2 | 8 |
| 319 | 4 | 2 | 9 |
| 320 | 4 | 2 | 10 |
| 321 | 4 | 3 | 1 |
| 322 | 4 | 3 | 2 |
| 323 | 4 | 3 | 3 |
| 324 | 4 | 3 | 4 |
| 325 | 4 | 3 | 5 |
| 326 | 4 | 3 | 6 |
| 327 | 4 | 3 | 7 |
| 328 | 4 | 3 | 8 |
| 329 | 4 | 3 | 9 |
| 330 | 4 | 3 | 10 |
| 331 | 4 | 4 | 1 |
| 332 | 4 | 4 | 2 |
| 333 | 4 | 4 | 3 |
| 334 | 4 | 4 | 4 |
| 335 | 4 | 4 | 5 |
| 336 | 4 | 4 | 6 |
| 337 | 4 | 4 | 7 |
| 338 | 4 | 4 | 8 |
| 339 | 4 | 4 | 9 |
| 340 | 4 | 4 | 10 |
| 341 | 4 | 5 | 1 |
| 342 | 4 | 5 | 2 |
| 343 | 4 | 5 | 3 |
| 344 | 4 | 5 | 4 |
| 345 | 4 | 5 | 5 |
| 346 | 4 | 5 | 6 |
| 347 | 4 | 5 | 7 |
| 348 | 4 | 5 | 8 |
| 349 | 4 | 5 | 9 |
| 350 | 4 | 5 | 10 |
| 351 | 4 | 6 | 1 |
| 352 | 4 | 6 | 2 |
| 353 | 4 | 6 | 3 |
| 354 | 4 | 6 | 4 |
| 355 | 4 | 6 | 5 |
| 356 | 4 | 6 | 6 |
| 357 | 4 | 6 | 7 |
| 358 | 4 | 6 | 8 |
| 359 | 4 | 6 | 9 |
| 360 | 4 | 6 | 10 |
| 361 | 4 | 7 | 1 |
| 362 | 4 | 7 | 2 |
| 363 | 4 | 7 | 3 |
| 364 | 4 | 7 | 4 |
| 365 | 4 | 7 | 5 |
| 366 | 4 | 7 | 6 |
| 367 | 4 | 7 | 7 |
| 368 | 4 | 7 | 8 |
| 369 | 4 | 7 | 9 |
| 370 | 4 | 7 | 10 |
| 371 | 4 | 8 | 1 |
| 372 | 4 | 8 | 2 |
| 373 | 4 | 8 | 3 |
| 374 | 4 | 8 | 4 |
| 375 | 4 | 8 | 5 |
| 376 | 4 | 8 | 6 |
| 377 | 4 | 8 | 7 |
| 378 | 4 | 8 | 8 |
| 379 | 4 | 8 | 9 |
| 380 | 4 | 8 | 10 |
| 381 | 4 | 9 | 1 |
| 382 | 4 | 9 | 2 |
| 383 | 4 | 9 | 3 |
| 384 | 4 | 9 | 4 |
| 385 | 4 | 9 | 5 |
| 386 | 4 | 9 | 6 |
| 387 | 4 | 9 | 7 |
| 388 | 4 | 9 | 8 |
| 389 | 4 | 9 | 9 |
| 390 | 4 | 9 | 10 |
| 391 | 4 | 10 | 1 |
| 392 | 4 | 10 | 2 |
| 393 | 4 | 10 | 3 |
| 394 | 4 | 10 | 4 |
| 395 | 4 | 10 | 5 |
| 396 | 4 | 10 | 6 |
| 397 | 4 | 10 | 7 |
| 398 | 4 | 10 | 8 |
| 399 | 4 | 10 | 9 |
| 400 | 4 | 10 | 10 |
| 401 | 5 | 1 | 1 |
| 402 | 5 | 1 | 2 |
| 403 | 5 | 1 | 3 |
| 404 | 5 | 1 | 4 |
| 405 | 5 | 1 | 5 |
| 406 | 5 | 1 | 6 |
| 407 | 5 | 1 | 7 |
| 408 | 5 | 1 | 8 |
| 409 | 5 | 1 | 9 |

TABLE X-continued

| # | A | B | C |
|---|---|---|---|
| 410 | 5 | 1 | 10 |
| 411 | 5 | 2 | 1 |
| 412 | 5 | 2 | 2 |
| 413 | 5 | 2 | 3 |
| 414 | 5 | 2 | 4 |
| 415 | 5 | 2 | 5 |
| 416 | 5 | 2 | 6 |
| 417 | 5 | 2 | 7 |
| 418 | 5 | 2 | 8 |
| 419 | 5 | 2 | 9 |
| 420 | 5 | 2 | 10 |
| 421 | 5 | 3 | 1 |
| 422 | 5 | 3 | 2 |
| 423 | 5 | 3 | 3 |
| 424 | 5 | 3 | 4 |
| 425 | 5 | 3 | 5 |
| 426 | 5 | 3 | 6 |
| 427 | 5 | 3 | 7 |
| 428 | 5 | 3 | 8 |
| 429 | 5 | 3 | 9 |
| 430 | 5 | 3 | 10 |
| 431 | 5 | 4 | 1 |
| 432 | 5 | 4 | 2 |
| 433 | 5 | 4 | 3 |
| 434 | 5 | 4 | 4 |
| 435 | 5 | 4 | 5 |
| 436 | 5 | 4 | 6 |
| 437 | 5 | 4 | 7 |
| 438 | 5 | 4 | 8 |
| 439 | 5 | 4 | 9 |
| 440 | 5 | 4 | 10 |
| 441 | 5 | 5 | 1 |
| 442 | 5 | 5 | 2 |
| 443 | 5 | 5 | 3 |
| 444 | 5 | 5 | 4 |
| 445 | 5 | 5 | 5 |
| 446 | 5 | 5 | 6 |
| 447 | 5 | 5 | 7 |
| 448 | 5 | 5 | 8 |
| 449 | 5 | 5 | 9 |
| 450 | 5 | 5 | 10 |
| 451 | 5 | 6 | 1 |
| 452 | 5 | 6 | 2 |
| 453 | 5 | 6 | 3 |
| 454 | 5 | 6 | 4 |
| 455 | 5 | 6 | 5 |
| 456 | 5 | 6 | 6 |
| 457 | 5 | 6 | 7 |
| 458 | 5 | 6 | 8 |
| 459 | 5 | 6 | 9 |
| 460 | 5 | 6 | 10 |
| 461 | 5 | 7 | 1 |
| 462 | 5 | 7 | 2 |
| 463 | 5 | 7 | 3 |
| 464 | 5 | 7 | 4 |
| 465 | 5 | 7 | 5 |
| 466 | 5 | 7 | 6 |
| 467 | 5 | 7 | 7 |
| 468 | 5 | 7 | 8 |
| 469 | 5 | 7 | 9 |
| 470 | 5 | 7 | 10 |
| 471 | 5 | 8 | 1 |
| 472 | 5 | 8 | 2 |
| 473 | 5 | 8 | 3 |
| 474 | 5 | 8 | 4 |
| 475 | 5 | 8 | 5 |
| 476 | 5 | 8 | 6 |
| 477 | 5 | 8 | 7 |
| 478 | 5 | 8 | 8 |
| 479 | 5 | 8 | 9 |
| 480 | 5 | 8 | 10 |
| 481 | 5 | 9 | 1 |
| 482 | 5 | 9 | 2 |
| 483 | 5 | 9 | 3 |
| 484 | 5 | 9 | 4 |
| 485 | 5 | 9 | 5 |
| 486 | 5 | 9 | 6 |
| 487 | 5 | 9 | 7 |
| 488 | 5 | 9 | 8 |
| 489 | 5 | 9 | 9 |
| 490 | 5 | 9 | 10 |
| 491 | 5 | 10 | 1 |
| 492 | 5 | 10 | 2 |
| 493 | 5 | 10 | 3 |
| 494 | 5 | 10 | 4 |
| 495 | 5 | 10 | 5 |
| 496 | 5 | 10 | 6 |
| 497 | 5 | 10 | 7 |
| 498 | 5 | 10 | 8 |
| 499 | 5 | 10 | 9 |
| 500 | 5 | 10 | 10 |
| 501 | 6 | 1 | 1 |
| 502 | 6 | 1 | 2 |
| 503 | 6 | 1 | 3 |
| 504 | 6 | 1 | 4 |
| 505 | 6 | 1 | 5 |
| 506 | 6 | 1 | 6 |
| 507 | 6 | 1 | 7 |
| 508 | 6 | 1 | 8 |
| 509 | 6 | 1 | 9 |
| 510 | 6 | 1 | 10 |
| 511 | 6 | 2 | 1 |
| 512 | 6 | 2 | 2 |
| 513 | 6 | 2 | 3 |
| 514 | 6 | 2 | 4 |
| 515 | 6 | 2 | 5 |
| 516 | 6 | 2 | 6 |
| 517 | 6 | 2 | 7 |
| 518 | 6 | 2 | 8 |
| 519 | 6 | 2 | 9 |
| 520 | 6 | 2 | 10 |
| 521 | 6 | 3 | 1 |
| 522 | 6 | 3 | 2 |
| 523 | 6 | 3 | 3 |
| 524 | 6 | 3 | 4 |
| 525 | 6 | 3 | 5 |
| 526 | 6 | 3 | 6 |
| 527 | 6 | 3 | 7 |
| 528 | 6 | 3 | 8 |
| 529 | 6 | 3 | 9 |
| 530 | 6 | 3 | 10 |
| 531 | 6 | 4 | 1 |
| 532 | 6 | 4 | 2 |
| 533 | 6 | 4 | 3 |
| 534 | 6 | 4 | 4 |
| 535 | 6 | 4 | 5 |
| 536 | 6 | 4 | 6 |
| 537 | 6 | 4 | 7 |
| 538 | 6 | 4 | 8 |
| 539 | 6 | 4 | 9 |
| 540 | 6 | 4 | 10 |
| 541 | 6 | 5 | 1 |
| 542 | 6 | 5 | 2 |
| 543 | 6 | 5 | 3 |
| 544 | 6 | 5 | 4 |
| 545 | 6 | 5 | 5 |
| 546 | 6 | 5 | 6 |
| 547 | 6 | 5 | 7 |
| 548 | 6 | 5 | 8 |
| 549 | 6 | 5 | 9 |
| 550 | 6 | 5 | 10 |
| 551 | 6 | 6 | 1 |
| 552 | 6 | 6 | 2 |
| 553 | 6 | 6 | 3 |
| 554 | 6 | 6 | 4 |
| 555 | 6 | 6 | 5 |
| 556 | 6 | 6 | 6 |
| 557 | 6 | 6 | 7 |
| 558 | 6 | 6 | 8 |
| 559 | 6 | 6 | 9 |
| 560 | 6 | 6 | 10 |
| 561 | 6 | 7 | 1 |
| 562 | 6 | 7 | 2 |
| 563 | 6 | 7 | 3 |
| 564 | 6 | 7 | 4 |
| 565 | 6 | 7 | 5 |

TABLE X-continued

| # | A | B | C |
|---|---|---|---|
| 566 | 6 | 7 | 6 |
| 567 | 6 | 7 | 7 |
| 568 | 6 | 7 | 8 |
| 569 | 6 | 7 | 9 |
| 570 | 6 | 7 | 10 |
| 571 | 6 | 8 | 1 |
| 572 | 6 | 8 | 2 |
| 573 | 6 | 8 | 3 |
| 574 | 6 | 8 | 4 |
| 575 | 6 | 8 | 5 |
| 576 | 6 | 8 | 6 |
| 577 | 6 | 8 | 7 |
| 578 | 6 | 8 | 8 |
| 579 | 6 | 8 | 9 |
| 580 | 6 | 8 | 10 |
| 581 | 6 | 9 | 1 |
| 582 | 6 | 9 | 2 |
| 583 | 6 | 9 | 3 |
| 584 | 6 | 9 | 4 |
| 585 | 6 | 9 | 5 |
| 586 | 6 | 9 | 6 |
| 587 | 6 | 9 | 7 |
| 588 | 6 | 9 | 8 |
| 589 | 6 | 9 | 9 |
| 590 | 6 | 9 | 10 |
| 591 | 6 | 10 | 1 |
| 592 | 6 | 10 | 2 |
| 593 | 6 | 10 | 3 |
| 594 | 6 | 10 | 4 |
| 595 | 6 | 10 | 5 |
| 596 | 6 | 10 | 6 |
| 597 | 6 | 10 | 7 |
| 598 | 6 | 10 | 8 |
| 599 | 6 | 10 | 9 |
| 600 | 6 | 10 | 10 |
| 601 | 7 | 1 | 1 |
| 602 | 7 | 1 | 2 |
| 603 | 7 | 1 | 3 |
| 604 | 7 | 1 | 4 |
| 605 | 7 | 1 | 5 |
| 606 | 7 | 1 | 6 |
| 607 | 7 | 1 | 7 |
| 608 | 7 | 1 | 8 |
| 609 | 7 | 1 | 9 |
| 610 | 7 | 1 | 10 |
| 611 | 7 | 2 | 1 |
| 612 | 7 | 2 | 2 |
| 613 | 7 | 2 | 3 |
| 614 | 7 | 2 | 4 |
| 615 | 7 | 2 | 5 |
| 616 | 7 | 2 | 6 |
| 617 | 7 | 2 | 7 |
| 618 | 7 | 2 | 8 |
| 619 | 7 | 2 | 9 |
| 620 | 7 | 2 | 10 |
| 621 | 7 | 3 | 1 |
| 622 | 7 | 3 | 2 |
| 623 | 7 | 3 | 3 |
| 624 | 7 | 3 | 4 |
| 625 | 7 | 3 | 5 |
| 626 | 7 | 3 | 6 |
| 627 | 7 | 3 | 7 |
| 628 | 7 | 3 | 8 |
| 629 | 7 | 3 | 9 |
| 630 | 7 | 3 | 10 |
| 631 | 7 | 4 | 1 |
| 632 | 7 | 4 | 2 |
| 633 | 7 | 4 | 3 |
| 634 | 7 | 4 | 4 |
| 635 | 7 | 4 | 5 |
| 636 | 7 | 4 | 6 |
| 637 | 7 | 4 | 7 |
| 638 | 7 | 4 | 8 |
| 639 | 7 | 4 | 9 |
| 640 | 7 | 4 | 10 |
| 641 | 7 | 5 | 1 |
| 642 | 7 | 5 | 2 |
| 643 | 7 | 5 | 3 |
| 644 | 7 | 5 | 4 |
| 645 | 7 | 5 | 5 |
| 646 | 7 | 5 | 6 |
| 647 | 7 | 5 | 7 |
| 648 | 7 | 5 | 8 |
| 649 | 7 | 5 | 9 |
| 650 | 7 | 5 | 10 |
| 651 | 7 | 6 | 1 |
| 652 | 7 | 6 | 2 |
| 653 | 7 | 6 | 3 |
| 654 | 7 | 6 | 4 |
| 655 | 7 | 6 | 5 |
| 656 | 7 | 6 | 6 |
| 657 | 7 | 6 | 7 |
| 658 | 7 | 6 | 8 |
| 659 | 7 | 6 | 9 |
| 660 | 7 | 6 | 10 |
| 661 | 7 | 7 | 1 |
| 662 | 7 | 7 | 2 |
| 663 | 7 | 7 | 3 |
| 664 | 7 | 7 | 4 |
| 665 | 7 | 7 | 5 |
| 666 | 7 | 7 | 6 |
| 667 | 7 | 7 | 7 |
| 668 | 7 | 7 | 8 |
| 669 | 7 | 7 | 9 |
| 670 | 7 | 7 | 10 |
| 671 | 7 | 8 | 1 |
| 672 | 7 | 8 | 2 |
| 673 | 7 | 8 | 3 |
| 674 | 7 | 8 | 4 |
| 675 | 7 | 8 | 5 |
| 676 | 7 | 8 | 6 |
| 677 | 7 | 8 | 7 |
| 678 | 7 | 8 | 8 |
| 679 | 7 | 8 | 9 |
| 680 | 7 | 8 | 10 |
| 681 | 7 | 9 | 1 |
| 682 | 7 | 9 | 2 |
| 683 | 7 | 9 | 3 |
| 684 | 7 | 9 | 4 |
| 685 | 7 | 9 | 5 |
| 686 | 7 | 9 | 6 |
| 687 | 7 | 9 | 7 |
| 688 | 7 | 9 | 8 |
| 689 | 7 | 9 | 9 |
| 690 | 7 | 9 | 10 |
| 691 | 7 | 10 | 1 |
| 692 | 7 | 10 | 2 |
| 693 | 7 | 10 | 3 |
| 694 | 7 | 10 | 4 |
| 695 | 7 | 10 | 5 |
| 696 | 7 | 10 | 6 |
| 697 | 7 | 10 | 7 |
| 698 | 7 | 10 | 8 |
| 699 | 7 | 10 | 9 |
| 700 | 7 | 10 | 10 |
| 701 | 8 | 1 | 1 |
| 702 | 8 | 1 | 2 |
| 703 | 8 | 1 | 3 |
| 704 | 8 | 1 | 4 |
| 705 | 8 | 1 | 5 |
| 706 | 8 | 1 | 6 |
| 707 | 8 | 1 | 7 |
| 708 | 8 | 1 | 8 |
| 709 | 8 | 1 | 9 |
| 710 | 8 | 1 | 10 |
| 711 | 8 | 2 | 1 |
| 712 | 8 | 2 | 2 |
| 713 | 8 | 2 | 3 |
| 714 | 8 | 2 | 4 |
| 715 | 8 | 2 | 5 |
| 716 | 8 | 2 | 6 |
| 717 | 8 | 2 | 7 |
| 718 | 8 | 2 | 8 |
| 719 | 8 | 2 | 9 |
| 720 | 8 | 2 | 10 |
| 721 | 8 | 3 | 1 |

TABLE X-continued

| # | A | B | C |
|---|---|---|---|
| 722 | 8 | 3 | 2 |
| 723 | 8 | 3 | 3 |
| 724 | 8 | 3 | 4 |
| 725 | 8 | 3 | 5 |
| 726 | 8 | 3 | 6 |
| 727 | 8 | 3 | 7 |
| 728 | 8 | 3 | 8 |
| 729 | 8 | 3 | 9 |
| 730 | 8 | 3 | 10 |
| 731 | 8 | 4 | 1 |
| 732 | 8 | 4 | 2 |
| 733 | 8 | 4 | 3 |
| 734 | 8 | 4 | 4 |
| 735 | 8 | 4 | 5 |
| 736 | 8 | 4 | 6 |
| 737 | 8 | 4 | 7 |
| 738 | 8 | 4 | 8 |
| 739 | 8 | 4 | 9 |
| 740 | 8 | 4 | 10 |
| 741 | 8 | 5 | 1 |
| 742 | 8 | 5 | 2 |
| 743 | 8 | 5 | 3 |
| 744 | 8 | 5 | 4 |
| 745 | 8 | 5 | 5 |
| 746 | 8 | 5 | 6 |
| 747 | 8 | 5 | 7 |
| 748 | 8 | 5 | 8 |
| 749 | 8 | 5 | 9 |
| 750 | 8 | 5 | 10 |
| 751 | 8 | 6 | 1 |
| 752 | 8 | 6 | 2 |
| 753 | 8 | 6 | 3 |
| 754 | 8 | 6 | 4 |
| 755 | 8 | 6 | 5 |
| 756 | 8 | 6 | 6 |
| 757 | 8 | 6 | 7 |
| 758 | 8 | 6 | 8 |
| 759 | 8 | 6 | 9 |
| 760 | 8 | 6 | 10 |
| 761 | 8 | 7 | 1 |
| 762 | 8 | 7 | 2 |
| 763 | 8 | 7 | 3 |
| 764 | 8 | 7 | 4 |
| 765 | 8 | 7 | 5 |
| 766 | 8 | 7 | 6 |
| 767 | 8 | 7 | 7 |
| 768 | 8 | 7 | 8 |
| 769 | 8 | 7 | 9 |
| 770 | 8 | 7 | 10 |
| 771 | 8 | 8 | 1 |
| 772 | 8 | 8 | 2 |
| 773 | 8 | 8 | 3 |
| 774 | 8 | 8 | 4 |
| 775 | 8 | 8 | 5 |
| 776 | 8 | 8 | 6 |
| 777 | 8 | 8 | 7 |
| 778 | 8 | 8 | 8 |
| 779 | 8 | 8 | 9 |
| 780 | 8 | 8 | 10 |
| 781 | 8 | 9 | 1 |
| 782 | 8 | 9 | 2 |
| 783 | 8 | 9 | 3 |
| 784 | 8 | 9 | 4 |
| 785 | 8 | 9 | 5 |
| 786 | 8 | 9 | 6 |
| 787 | 8 | 9 | 7 |
| 788 | 8 | 9 | 8 |
| 789 | 8 | 9 | 9 |
| 790 | 8 | 9 | 10 |
| 791 | 8 | 10 | 1 |
| 792 | 8 | 10 | 2 |
| 793 | 8 | 10 | 3 |
| 794 | 8 | 10 | 4 |
| 795 | 8 | 10 | 5 |
| 796 | 8 | 10 | 6 |
| 797 | 8 | 10 | 7 |
| 798 | 8 | 10 | 8 |
| 799 | 8 | 10 | 9 |
| 800 | 8 | 10 | 10 |
| 801 | 9 | 1 | 1 |
| 802 | 9 | 1 | 2 |
| 803 | 9 | 1 | 3 |
| 804 | 9 | 1 | 4 |
| 805 | 9 | 1 | 5 |
| 806 | 9 | 1 | 6 |
| 807 | 9 | 1 | 7 |
| 808 | 9 | 1 | 8 |
| 809 | 9 | 1 | 9 |
| 810 | 9 | 1 | 10 |
| 811 | 9 | 2 | 1 |
| 812 | 9 | 2 | 2 |
| 813 | 9 | 2 | 3 |
| 814 | 9 | 2 | 4 |
| 815 | 9 | 2 | 5 |
| 816 | 9 | 2 | 6 |
| 817 | 9 | 2 | 7 |
| 818 | 9 | 2 | 8 |
| 819 | 9 | 2 | 9 |
| 820 | 9 | 2 | 10 |
| 821 | 9 | 3 | 1 |
| 822 | 9 | 3 | 2 |
| 823 | 9 | 3 | 3 |
| 824 | 9 | 3 | 4 |
| 825 | 9 | 3 | 5 |
| 826 | 9 | 3 | 6 |
| 827 | 9 | 3 | 7 |
| 828 | 9 | 3 | 8 |
| 829 | 9 | 3 | 9 |
| 830 | 9 | 3 | 10 |
| 831 | 9 | 4 | 1 |
| 832 | 9 | 4 | 2 |
| 833 | 9 | 4 | 3 |
| 834 | 9 | 4 | 4 |
| 835 | 9 | 4 | 5 |
| 836 | 9 | 4 | 6 |
| 837 | 9 | 4 | 7 |
| 838 | 9 | 4 | 8 |
| 839 | 9 | 4 | 9 |
| 840 | 9 | 4 | 10 |
| 841 | 9 | 5 | 1 |
| 842 | 9 | 5 | 2 |
| 843 | 9 | 5 | 3 |
| 844 | 9 | 5 | 4 |
| 845 | 9 | 5 | 5 |
| 846 | 9 | 5 | 6 |
| 847 | 9 | 5 | 7 |
| 848 | 9 | 5 | 8 |
| 849 | 9 | 5 | 9 |
| 850 | 9 | 5 | 10 |
| 851 | 9 | 6 | 1 |
| 852 | 9 | 6 | 2 |
| 853 | 9 | 6 | 3 |
| 854 | 9 | 6 | 4 |
| 855 | 9 | 6 | 5 |
| 856 | 9 | 6 | 6 |
| 857 | 9 | 6 | 7 |
| 858 | 9 | 6 | 8 |
| 859 | 9 | 6 | 9 |
| 860 | 9 | 6 | 10 |
| 861 | 9 | 7 | 1 |
| 862 | 9 | 7 | 2 |
| 863 | 9 | 7 | 3 |
| 864 | 9 | 7 | 4 |
| 865 | 9 | 7 | 5 |
| 866 | 9 | 7 | 6 |
| 867 | 9 | 7 | 7 |
| 868 | 9 | 7 | 8 |
| 869 | 9 | 7 | 9 |
| 870 | 9 | 7 | 10 |
| 871 | 9 | 8 | 1 |
| 872 | 9 | 8 | 2 |
| 873 | 9 | 8 | 3 |
| 874 | 9 | 8 | 4 |
| 875 | 9 | 8 | 5 |
| 876 | 9 | 8 | 6 |
| 877 | 9 | 8 | 7 |

TABLE X-continued

| # | A | B | C |
|---|---|---|---|
| 878 | 9 | 8 | 8 |
| 879 | 9 | 8 | 9 |
| 880 | 9 | 8 | 10 |
| 881 | 9 | 9 | 1 |
| 882 | 9 | 9 | 2 |
| 883 | 9 | 9 | 3 |
| 884 | 9 | 9 | 4 |
| 885 | 9 | 9 | 5 |
| 886 | 9 | 9 | 6 |
| 887 | 9 | 9 | 7 |
| 888 | 9 | 9 | 8 |
| 889 | 9 | 9 | 9 |
| 890 | 9 | 9 | 10 |
| 891 | 9 | 10 | 1 |
| 892 | 9 | 10 | 2 |
| 893 | 9 | 10 | 3 |
| 894 | 9 | 10 | 4 |
| 895 | 9 | 10 | 5 |
| 896 | 9 | 10 | 6 |
| 897 | 9 | 10 | 7 |
| 898 | 9 | 10 | 8 |
| 899 | 9 | 10 | 9 |
| 900 | 9 | 10 | 10 |
| 901 | 10 | 1 | 1 |
| 902 | 10 | 1 | 2 |
| 903 | 10 | 1 | 3 |
| 904 | 10 | 1 | 4 |
| 905 | 10 | 1 | 5 |
| 906 | 10 | 1 | 6 |
| 907 | 10 | 1 | 7 |
| 908 | 10 | 1 | 8 |
| 909 | 10 | 1 | 9 |
| 910 | 10 | 1 | 10 |
| 911 | 10 | 2 | 1 |
| 912 | 10 | 2 | 2 |
| 913 | 10 | 2 | 3 |
| 914 | 10 | 2 | 4 |
| 915 | 10 | 2 | 5 |
| 916 | 10 | 2 | 6 |
| 917 | 10 | 2 | 7 |
| 918 | 10 | 2 | 8 |
| 919 | 10 | 2 | 9 |
| 920 | 10 | 2 | 10 |
| 921 | 10 | 3 | 1 |
| 922 | 10 | 3 | 2 |
| 923 | 10 | 3 | 3 |
| 924 | 10 | 3 | 4 |
| 925 | 10 | 3 | 5 |
| 926 | 10 | 3 | 6 |
| 927 | 10 | 3 | 7 |
| 928 | 10 | 3 | 8 |
| 929 | 10 | 3 | 9 |
| 930 | 10 | 3 | 10 |
| 931 | 10 | 4 | 1 |
| 932 | 10 | 4 | 2 |
| 933 | 10 | 4 | 3 |
| 934 | 10 | 4 | 4 |
| 935 | 10 | 4 | 5 |
| 936 | 10 | 4 | 6 |
| 937 | 10 | 4 | 7 |
| 938 | 10 | 4 | 8 |
| 939 | 10 | 4 | 9 |
| 940 | 10 | 4 | 10 |
| 941 | 10 | 5 | 1 |
| 942 | 10 | 5 | 2 |
| 943 | 10 | 5 | 3 |
| 944 | 10 | 5 | 4 |
| 945 | 10 | 5 | 5 |
| 946 | 10 | 5 | 6 |
| 947 | 10 | 5 | 7 |
| 948 | 10 | 5 | 8 |
| 949 | 10 | 5 | 9 |
| 950 | 10 | 5 | 10 |
| 951 | 10 | 6 | 1 |
| 952 | 10 | 6 | 2 |
| 953 | 10 | 6 | 3 |
| 954 | 10 | 6 | 4 |
| 955 | 10 | 6 | 5 |
| 956 | 10 | 6 | 6 |
| 957 | 10 | 6 | 7 |
| 958 | 10 | 6 | 8 |
| 959 | 10 | 6 | 9 |
| 960 | 10 | 6 | 10 |
| 961 | 10 | 7 | 1 |
| 962 | 10 | 7 | 2 |
| 963 | 10 | 7 | 3 |
| 964 | 10 | 7 | 4 |
| 965 | 10 | 7 | 5 |
| 966 | 10 | 7 | 6 |
| 967 | 10 | 7 | 7 |
| 968 | 10 | 7 | 8 |
| 969 | 10 | 7 | 9 |
| 970 | 10 | 7 | 10 |
| 971 | 10 | 8 | 1 |
| 972 | 10 | 8 | 2 |
| 973 | 10 | 8 | 3 |
| 974 | 10 | 8 | 4 |
| 975 | 10 | 8 | 5 |
| 976 | 10 | 8 | 6 |
| 977 | 10 | 8 | 7 |
| 978 | 10 | 8 | 8 |
| 979 | 10 | 8 | 9 |
| 980 | 10 | 8 | 10 |
| 981 | 10 | 9 | 1 |
| 982 | 10 | 9 | 2 |
| 983 | 10 | 9 | 3 |
| 984 | 10 | 9 | 4 |
| 985 | 10 | 9 | 5 |
| 986 | 10 | 9 | 6 |
| 987 | 10 | 9 | 7 |
| 988 | 10 | 9 | 8 |
| 989 | 10 | 9 | 9 |
| 990 | 10 | 9 | 10 |
| 991 | 10 | 10 | 1 |
| 992 | 10 | 10 | 2 |
| 993 | 10 | 10 | 3 |
| 994 | 10 | 10 | 4 |
| 995 | 10 | 10 | 5 |
| 996 | 10 | 10 | 6 |
| 997 | 10 | 10 | 7 |
| 998 | 10 | 10 | 8 |
| 999 | 10 | 10 | 9 |

The invention claimed is:

1. A method of promoting nerve growth, comprising administering a composition comprising alpha-ketoglutaric acid or a pharmaceutically acceptable salt thereof (AKG), and a lipase, a protease and an amylase to a subject in need thereof.

2. The method of treatment according to claim 1, wherein the treatment comprises administering an amount of the composition containing 0.1-30 g AKG to a patient per day.

3. The method of treatment according to claim 1, wherein the composition comprises 3000-300000 USP units of *Burkholderia cepacia* lipase per g AKG, 2000-200000 USP units of *Aspergillus melleus* protease per g AKG, and 300-30000 USP units of *Aspergillus oryzae* amylase per g AKG.

4. The method of treatment according to claim 1, wherein the lipase is selected from the group consisting of a mammalian lipase, a microbial lipase, a bacterial lipase, a pancrelipase lipase, a liprotamase lipase, a *Pseudomonas* lipase, a human or other mammalian bile-salt stimulated lipase (BSSL), a human or other mammalian bile-salt dependent lipase (BSDL), a *Rhizopus oryzae* lipase, a *Chromobacterium viscosum* lipase, a *Rhizopus delemar* lipase, a *Burkholderia* lipase, a *Burkholderia cepacia* lipase, and a *Burkholderia cepacia* lipase as cross-linked lipase crystals.

5. The method of treatment according to claim 1, wherein the protease is selected from the group consisting of a mammalian protease, a microbial protease, a fungal protease, a pancrelipase protease, a liprotamase protease, an *Aspergillus* protease and an *Aspergillus melleus* protease.

6. The method of treatment according to claim 1, wherein the amylase is selected from the group consisting of a mammalian amylase, a microbial amylase, a fungal amylase, a pancrelipase amylase, a liprotamase amylase, an *Aspergillus* amylase and *Aspergillus oryzae* amylase.

7. The method of claim 1, wherein the number of nerve cells is increased.

* * * * *